(12) United States Patent
Fout

(10) Patent No.: US 8,251,932 B2
(45) Date of Patent: Aug. 28, 2012

(54) ORTHOPEDIC WALKER BOOT HAVING AN INFLATABLE BLADDER

(75) Inventor: James M. Fout, Oceanside, CA (US)

(73) Assignee: Breg, Inc., Carlsbad, CA (US)

( * ) Notice: Subject to any disclaimer, the term of this patent is extended or adjusted under 35 U.S.C. 154(b) by 430 days.

(21) Appl. No.: 12/506,266

(22) Filed: Jul. 21, 2009

(65) Prior Publication Data

US 2010/0100018 A1    Apr. 22, 2010

Related U.S. Application Data

(60) Provisional application No. 61/196,879, filed on Oct. 20, 2008.

(51) Int. Cl.
*A61F 5/00* (2006.01)
*A43B 7/14* (2006.01)
(52) U.S. Cl. ............................ 602/13; 36/169
(58) Field of Classification Search .................... 602/13, 602/5, 1, 23, 24, 25, 27, 28, 29, 32; 36/1.5, 36/83, 117.1, 140, 169
See application file for complete search history.

(56) References Cited

U.S. PATENT DOCUMENTS

| | | |
|---|---|---|
| 3,745,998 A | 7/1973 | Rose |
| 3,955,565 A | 5/1976 | Johnson, Jr. |
| 4,057,056 A | 11/1977 | Payton |
| 4,572,169 A | 2/1986 | Mauldin et al. |
| 4,590,932 A | 5/1986 | Wilkerson |
| 4,771,768 A | 9/1988 | Crispin |
| 5,050,620 A | 9/1991 | Cooper |
| 5,078,128 A | 1/1992 | Grim et al. |
| 5,088,479 A | 2/1992 | Detoro |
| RE34,661 E * | 7/1994 | Grim .............................. 602/27 |
| 5,329,705 A | 7/1994 | Grim et al. |
| 5,378,223 A | 1/1995 | Grim et al. |
| 5,464,385 A * | 11/1995 | Grim .............................. 602/27 |
| 5,577,998 A | 11/1996 | Johnson, Jr. et al. |
| 5,713,143 A | 2/1998 | Kendall |
| 5,762,622 A | 6/1998 | Lamont |
| 5,891,073 A | 4/1999 | Deirmendjian et al. |
| 5,957,872 A | 9/1999 | Flick |
| 6,056,712 A | 5/2000 | Grim |
| 6,251,065 B1 | 6/2001 | Kochamba et al. |
| 6,277,087 B1 | 8/2001 | Hess et al. |
| 6,514,222 B2 | 2/2003 | Cook |

(Continued)

OTHER PUBLICATIONS

Sroufe Healthcare Products Inc., "Pneu Gel Chevron Walking Boot", at least as early as 2003-05-00.

(Continued)

*Primary Examiner* — Patricia Bianco
*Assistant Examiner* — Tarla Patel
(74) *Attorney, Agent, or Firm* — Rodney F. Brown

(57) ABSTRACT

An orthopedic walker boot for wearing on a lower limb of a wearer has a rigid external shell and a pliant internal boot received within the external shell. The internal boot includes a leg panel having an inflatable bladder and a pump panel having a pump for inflating the bladder. The leg panel is configured to wrap around a leg of a wearer and the external shell is sized and configured to receive the internal boot with the leg of the wearer wrapped therein. The pump panel has a first end fixably attached to the leg panel and has a selective and releasable operational orientation, wherein the pump panel is in an overlapping outer position relative to the leg panel.

17 Claims, 17 Drawing Sheets

U.S. PATENT DOCUMENTS

| | | |
|---|---|---|
| 6,554,785 B1 * | 4/2003 | Sroufe et al. .................... 602/23 |
| 6,558,339 B1 | 5/2003 | Graham |
| 6,755,798 B2 | 6/2004 | McCarthy et al. |
| 6,866,043 B1 | 3/2005 | Davis |
| 6,905,456 B1 * | 6/2005 | Brunner et al. ................. 600/16 |
| 6,926,687 B2 | 8/2005 | Shields |
| 2002/0083618 A1 | 7/2002 | Erickson et al. |
| 2002/0138026 A1 | 9/2002 | Cook |
| 2005/0070833 A1 | 3/2005 | Shields |
| 2005/0228332 A1 | 10/2005 | Bushby |
| 2005/0240139 A1 | 10/2005 | Bushby |

OTHER PUBLICATIONS

Aircast Incorporated. "Pneumatic Walker Diabetic System". Oct. 10, 2000.

Donjoy. "MaxTrac Air Walker", at least as early as Jul. 30, 2009.

* cited by examiner

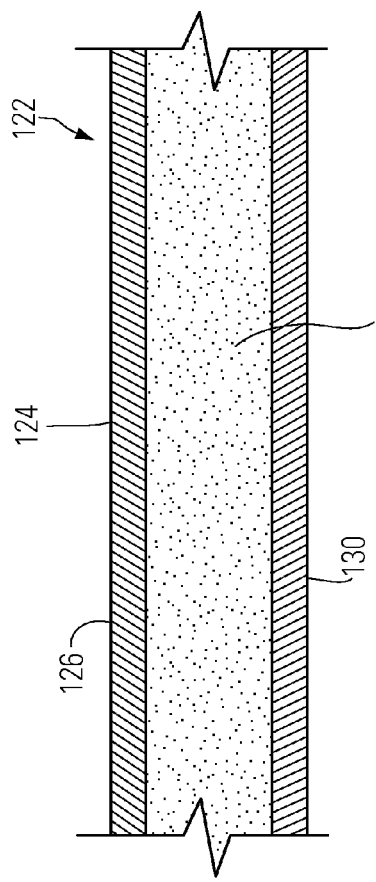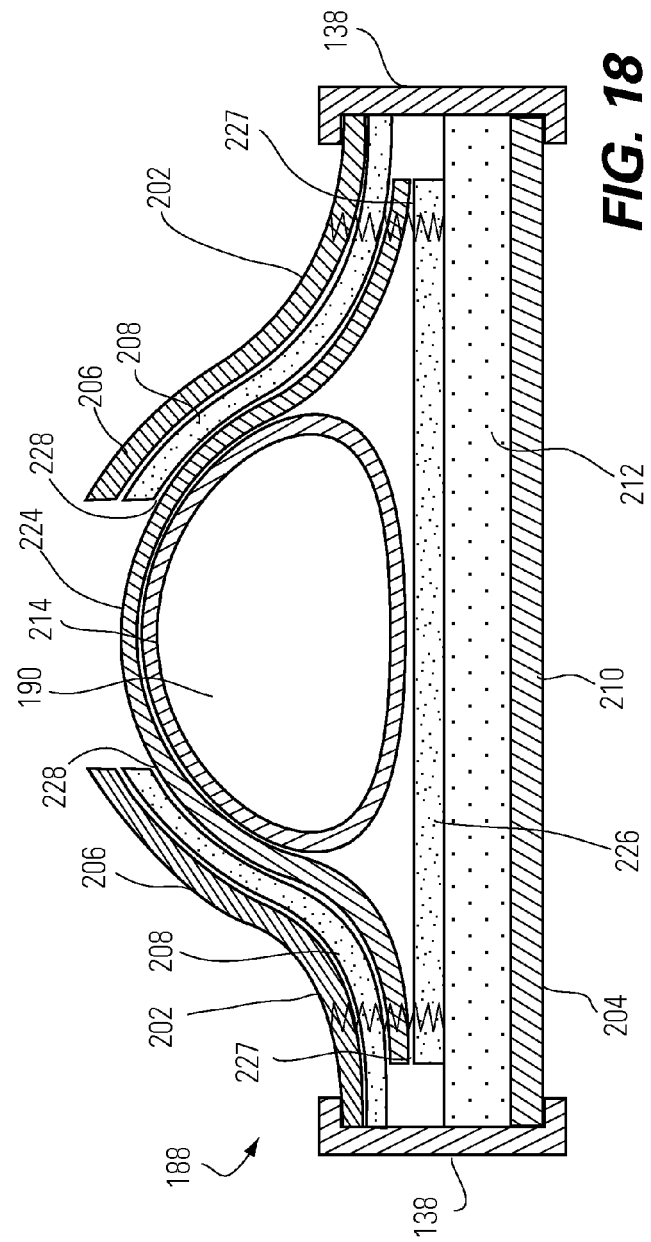

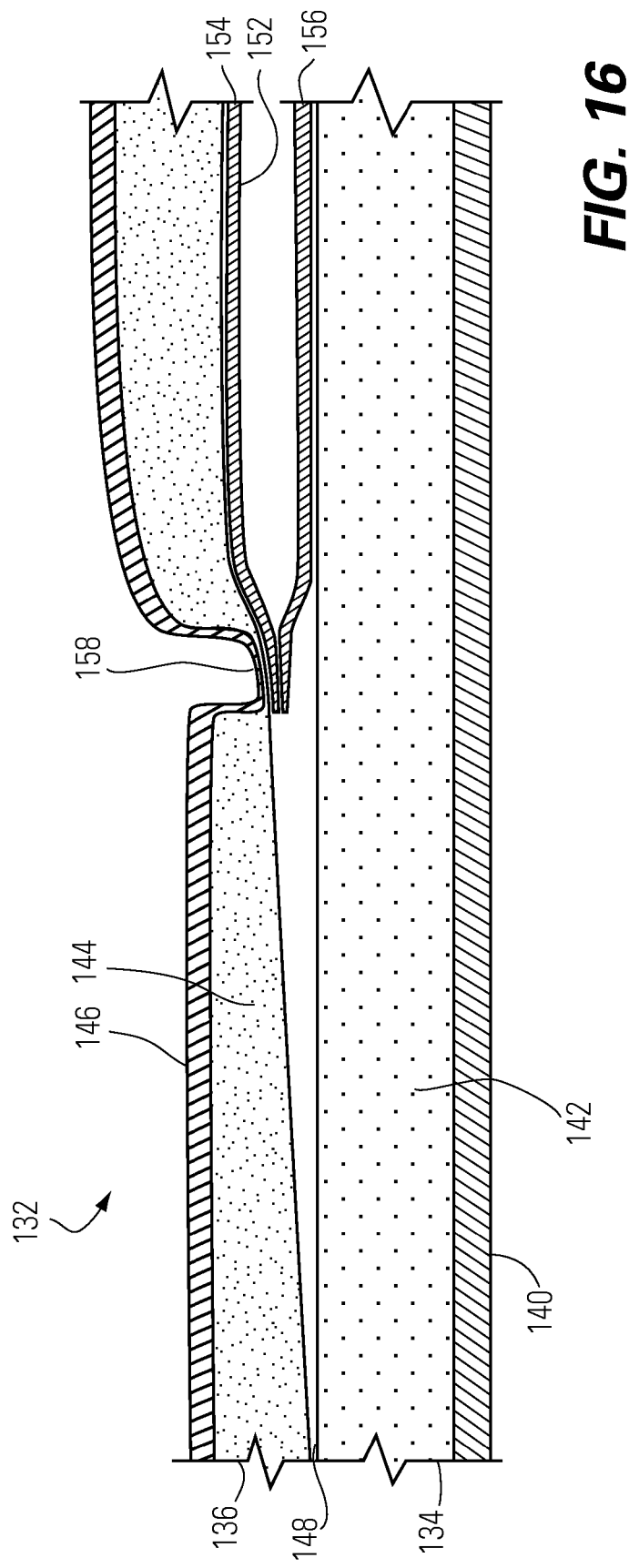

ORTHOPEDIC WALKER BOOT HAVING AN INFLATABLE BLADDER

This application claims the benefit of U.S. Provisional Application No. 61/196,879 filed on Oct. 20, 2008 entitled "Orthopedic Walker Having Removable Heal Plate", which is incorporated herein by reference.

BACKGROUND OF THE INVENTION

The present invention relates generally to orthopedic devices, and more particularly to orthopedic walker boots for supporting and/or immobilizing the lower limb of a wearer during activity.

Orthopedic walker boots are designed to be worn on the lower limb of a person afflicted with a lower leg, ankle, or foot injury, such as a fracture, soft tissue injury, or the like. The walker boot immobilizes and supports the injured lower limb during low-impact, weight-bearing activities such as walking and standing. The walker boot is often an effective substitute for a conventional plaster or fiberglass cast with numerous advantages. Among its advantages, walker boots are prefabricated yet are adaptable to different sized individual wearers or to variations in size of the same lower limb of a wearer over time as the lower limb is rehabilitated. In addition walker boots are more wear resistant, more comfortable to wear, and more easily cleaned than conventional casts and can be temporarily removed by the wearer for bathing, sleeping, range of motion exercise, or other non-weight-bearing activities.

Many orthopedic walker boots are known in the prior art. One such prior art orthopedic walker boot is disclosed in U.S. Pat. No. 5,078,128 to Grim et al. The walker boot of Grim et al. is characterized as having a soft goods-type support and a rigid frame. An injured lower limb is disposed in the soft goods-type support and the frame receives the soft goods-type support and lower limb disposed therein. In certain embodiments of Grim et al., one or more additional resilient support members can be included within the walker boot to supplement the function of the soft goods-type support. The resilient support members are inflatable bladders which are removably and/or adjustably mounted to the soft goods-type support between the support and the lower limb disposed therein. Removable and/or adjustable mounting of the bladders is effected by means of VELCRO hook and loop fasteners.

Each bladder of Grim et al. has a fill tube to which a portable squeeze pump can be selectively attached. Once the walker boot is secured to the lower limb, the practitioner accesses the fill tube of a first selected bladder of the walker boot and attaches the portable squeeze pump thereto. The practitioner squeezes the portable squeeze pump a sufficient number of times to inflate the bladder with an amount of air enabling the bladder to perform its desired support function. Once the bladder is properly inflated, the practitioner removes the portable squeeze pump from the fill tube and accesses the fill tube of the next bladder of the walker boot. The practitioner repeats this inflation procedure with respect to the next bladder and each succeeding bladder of the walker boot until all of the bladders are properly inflated. The practitioner then stores the portable squeeze pump apart from the walker boot until the practitioner desires to reinflate one or more of the bladders in the walker boot at some later time.

The present invention recognizes a need for an orthopedic walker boot having an inflatable bladder and a pump for the bladder which is integrally retained with the walker boot so that the pump is always readily available and accessible enabling inflation of the bladder whenever and/or wherever desired. Accordingly, it is an object of the present invention to provide an improved orthopedic walker boot having an inflatable bladder and a pump which is integrally retained with the walker boot at all times. It is another object of the present invention to provide an orthopedic walker boot having an inflatable bladder and a pump which is readily accessible to the wearer or any other practitioner at all times when the walker boot is being worn on the lower limb of the wearer. It is yet another object of the present invention to provide an orthopedic walker boot having an inflatable bladder and a pump which is integrally retained with the walker boot at all times yet does not substantially interfere with the desired function of the walker boot and/or impede the everyday activity of the wearer.

These objects and others are accomplished in accordance with the invention described hereafter.

SUMMARY OF THE INVENTION

One characterization of the present invention is an orthopedic walker boot including an external shell and an internal boot. The internal boot includes a leg panel having an inflatable bladder and a pump panel having a pump for inflating the bladder. The leg panel is configured to wrap around a leg of a wearer and the external shell is sized and configured to receive the internal boot with the leg of the wearer wrapped therein. The pump panel is configured with a first end and a second end. The first end is fixably attached to the leg panel. The pump panel has a selective and releasable operational orientation when the internal boot is received within the external shell. The pump panel is in an overlapping outer position relative to the leg panel when the pump panel is in the operational orientation.

In accordance with certain specific embodiments of the invention, the pump panel has a relatively narrow elongate linear configuration and the leg panel has a relatively broad areal configuration. The pump panel is fixably attached to an upper portion of the leg panel and extends from the upper portion when the pump panel is in a non-operational orientation with the second end free. The external shell is substantially rigid, but includes a non-rigid retention strap. The bladder is integrally formed with the remainder of the leg panel. More specifically, the bladder and a cloth and foam laminate sheet are integrally welded together in the leg panel.

In accordance with other specific embodiments of the invention, the second end of the pump panel is selectively releasably attached to the leg panel when the pump panel is in the operational orientation. Alternatively, the second end of the pump panel is selectively releasably attached to the leg panel or the external shell when the pump panel is in the operational orientation. The pump panel is also in an overlapping outer position relative to the external shell when the pump panel is in the operational orientation. More specifically, the pump panel is also in an overlapping outer position relative to the retention strap of the external shell when the pump panel is in the operational orientation.

Another characterization of the present invention is an orthopedic walker boot including an external shell and an internal boot. The internal boot has a closed on-the-leg configuration and includes a leg panel having an inflatable bladder and a pump panel having a pump for inflating the bladder. The leg panel is configured to wrap around a leg of a wearer when the internal boot is in the closed on-the-leg configuration. The pump panel is configured with a first end and a second end. The first end is fixably attached to the leg panel.

The external shell is sized and configured to receive the internal boot when in the closed on-the-leg configuration. The second end of the pump panel is free when the pump panel is in a non-operational orientation. The pump panel is placed in an operational orientation by selectively and releasably attaching the second end of the pump panel to the leg panel or the external shell when the leg panel is in the closed on-the-leg configuration and the internal boot is received within the external shell. The pump panel is in an overlapping outer position relative to the leg panel when in the operational orientation.

Yet another characterization of the present invention is an orthopedic walker boot including an external shell and an internal boot. The internal boot includes a leg panel having an inflatable bladder and a pump panel having a pump for inflating the bladder. The leg panel is configured to wrap around a leg of a wearer and the pump panel is configured with a first end and a second end. The first end is fixably attached to the leg panel. The external shell is sized and configured to receive the internal boot. The pump panel is placed in an operational orientation by selectively and releasably attaching the second end of the pump panel to the leg panel or the external shell when the internal boot is received within the external shell. The pump panel is in an overlapping outer position relative to the leg panel when in the operational orientation.

The present invention will be further understood from the drawings and the following detailed description.

BRIEF DESCRIPTION OF THE DRAWINGS

The accompanying drawings illustrate certain aspects of the present invention, but should not be viewed as by themselves limiting or defining the invention.

FIG. 15 is a cross-sectional view of the sole panel of the internal boot of FIG. 14 which is taken along line 15-15.

FIG. 16 is a cross-sectional view of the leg panel of the internal boot of FIG. 14 which is taken along line 16-16.

FIG. 18 is a cross-sectional view of the pump panel of the internal boot of FIG. 14 which is taken along line 18-18.

DESCRIPTION OF PREFERRED EMBODIMENTS

Figure 1:
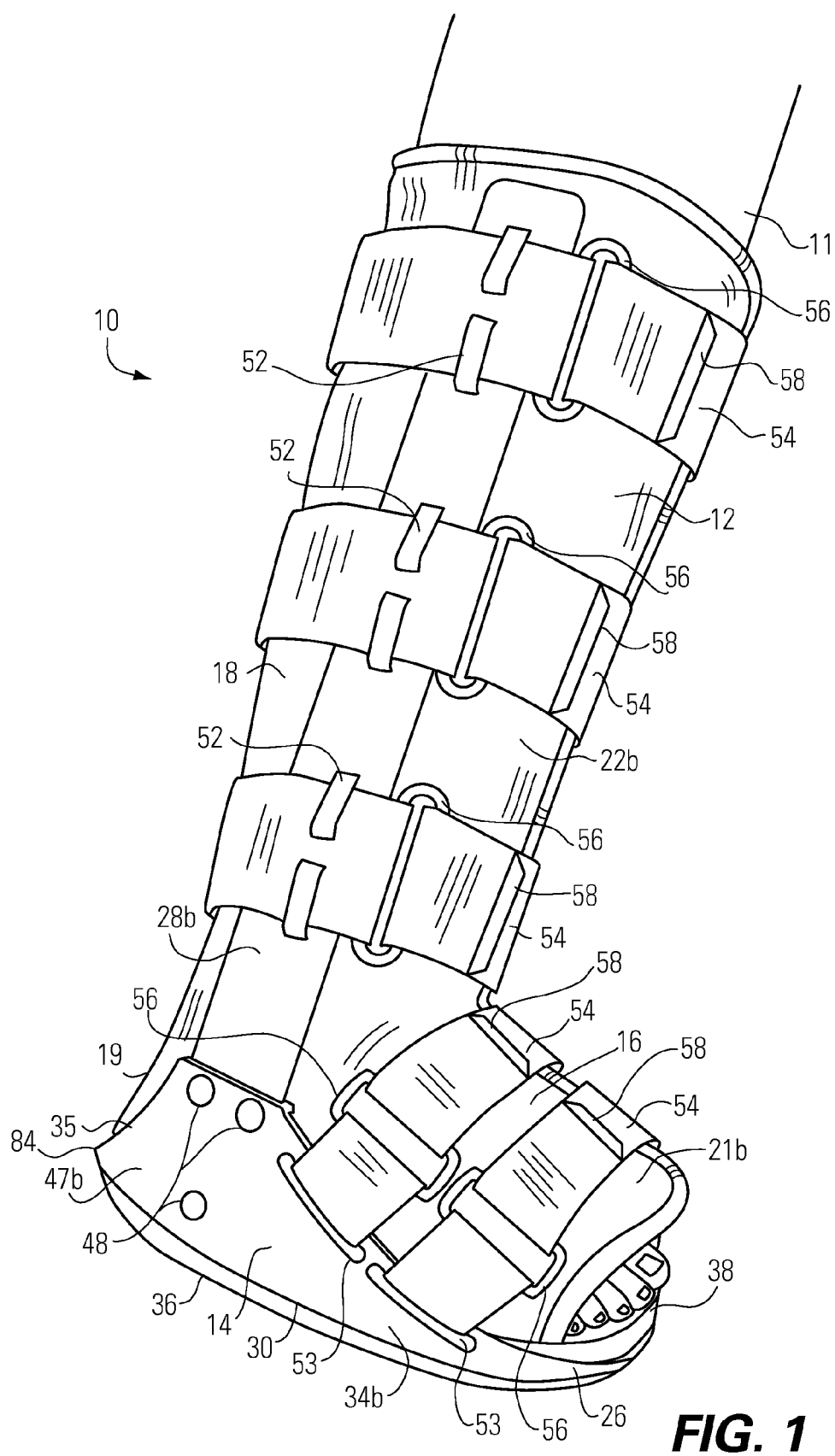
FIG. 1 is a side perspective view of an orthopedic walker boot of the present invention worn on a lower limb, wherein the orthopedic walker boot has an open-heel configuration.
Figure 2:
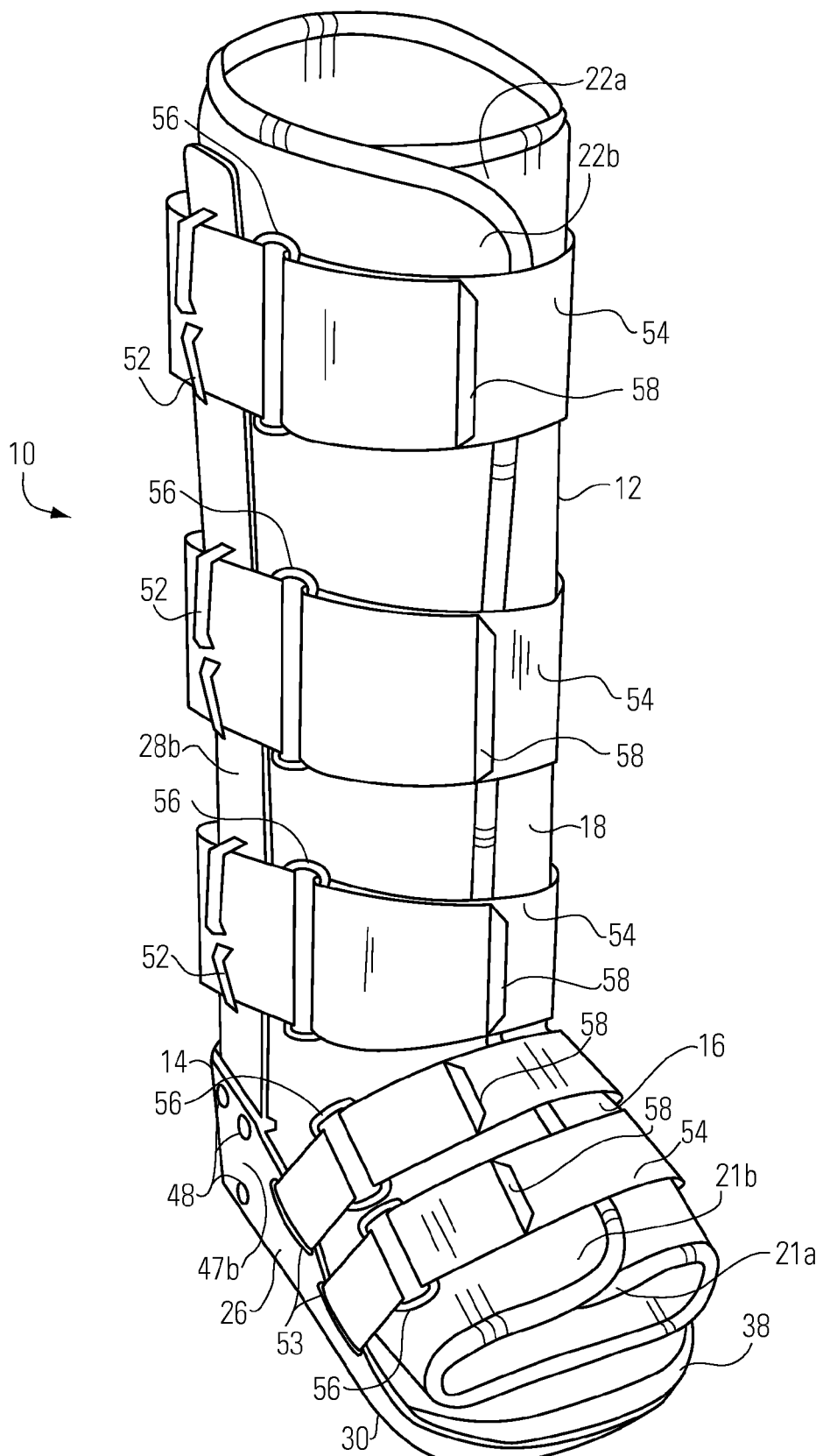
FIG. 2 is a front perspective view of the orthopedic walker boot of FIG. 1, wherein the lower limb of the wearer has been omitted for clarity.

Referring initially to FIGS. 1 and 2, an embodiment of the orthopedic walker boot of the present invention is shown and generally designated 10. The orthopedic walker boot 10 is generally sized and configured to be worn on a lower limb 11 of a person in the manner of conventional ankle-high or knee-high footwear as shown in FIG. 1. The lower limb 11 has been omitted from FIG. 2 for purposes of illustration, but it is understood that the same relationship shown in FIG. 1 between the orthopedic walker boot 10 and the lower limb 11 carries over to FIG. 2.

The orthopedic walker boot 10 comprises an internal boot 12 and an external shell 14. The internal boot 12 has a foot portion 16 which is configured to enclose the foot of the lower limb 11. As such, the foot portion 16 extends forward from the heel to the toes of the wearer's foot when the orthopedic walker boot 10 is worn on the lower limb 11. The internal boot 12 also has a lower leg portion 18 which is configured to enclose the lower leg, including the ankle, of the lower limb 11. As such, the lower leg portion 18 extends upward from the heel to a point proximal to, but below, the wearer's knee when the orthopedic walker boot 10 is worn on the lower limb 11. The internal boot 12 still further has a heel portion 19 at the intersection of the foot portion 16 and lower leg portion 18 which is configured to enclose the heel of the lower limb 11. As such, the heel portion 19 is positioned at the wearer's heel when the orthopedic walker boot 10 is worn on the lower limb 11.

FIGS. 1 and 2 show the internal boot 12 in a closed on-the-leg configuration. In accordance with the closed on-the-leg configuration, the internal boot 12 is open at its lower end to expose the toes on the foot of the lower limb 11 and at is upper end to expose the lower leg of the lower limb 11 proximal to, but below, the knee. However, the remainder of the internal boot 12, i.e., the foot, lower leg and heel portions 16, 18, and 19, which extend between the open ends of the internal boot 12, is essentially fully closed. As such, the internal boot 12 forms an essentially continuous enclosure for the lower limb 11 of the wearer when the internal boot 12 is in the closed on-the-leg configuration.

Figure 3:
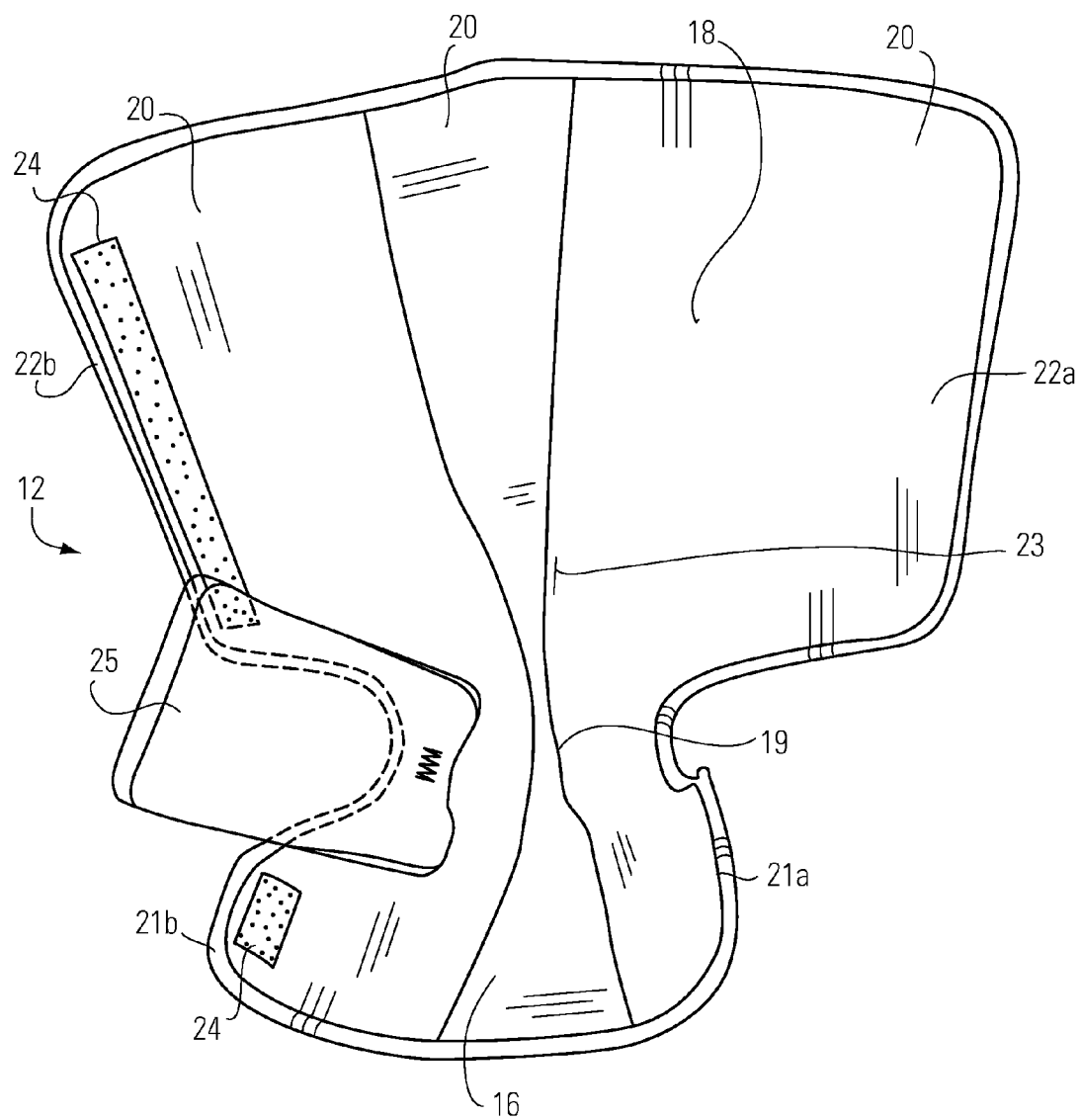
FIG. 3 is a front perspective view of an internal boot included in the orthopedic walker boot of FIG. 1, but with the internal boot having an off-the-leg configuration.

Details of the internal boot 12 are described below with reference to FIG. 3. It is noted that FIG. 3 shows the internal boot in an open off-the-leg configuration. The internal boot 12 is transitionable between the open off-the-leg configuration shown in FIG. 3 and the closed on-the-leg configuration shown in FIGS. 1 and 2 in a manner described hereafter.

The internal boot 12 is fabricated from one or more soft pliant materials, which insulate the enclosed lower limb 11 from direct contact with rigid objects external to the internal boot 12, thereby both cushioning and protecting the lower limb 11. A preferred soft pliant material for the internal boot 12 is a laminate. A laminate is defined herein as a unitary sheet formed from a plurality of planar layers of material overlaying and continuously and permanently bonded to one another across substantially their entire adjoining surfaces by means of an adhesive or the like. A preferred laminate is a cloth-foam-cloth laminate with the cloth forming the exposed faces of the laminate.

The internal boot 12 is constructed by cutting a sheet of the soft pliant material into a plurality panels 20 which are configured to conform to the dimensions of the lower limb 11 of the wearer when the panels are assembled together. Assembly of the panels 20 is effected by sewing the panels 20 together along their adjacent edges. The resulting internal boot 12 is preferably free of any supplemental support structures, such as stays, stiffeners, splints, fluid-filled bladders, or the like, which are integral with or mounted to the internal boot 12. Thus, the internal boot 12 preferably lacks any retention structures, such as stitching, pockets, straps, fasteners, or the like, which are adapted to retain any supplemental support structures.

The anterior of the internal boot 12 is provided with first and second lower flaps 21a, 21b, which are integrally configured with the foot portion 16 of the internal boot 12, and first and second upper flaps 22a, 22b, which are integrally configured with the lower leg portion 18 of the internal boot 12. The first and second lower flaps 21a, 21b and the first and second upper flaps 22a, 22b are selectively engagable with one another and disengagable from one another in a manner described hereafter. Selective engagement and disengagement of the first and second lower flaps 21a, 21b and the first and second upper flaps 22a, 22b enables the practitioner to transition the internal boot 12 between the closed on-the-leg configuration shown in FIGS. 1 and 2 and the open off-the-leg configuration shown in FIG. 3.

The internal boot 12 is preferably transitioned from the open off-the-leg configuration to the closed on-the-leg configuration after the lower limb 11 has been disposed in the interior 23 of the internal boot 12 while in the open off-the-leg configuration. The closed on-the-leg configuration is effected by overlapping the first lower flap 21a with the second lower flap 21b and correspondingly overlapping the first upper flap 22a with the second upper flap 22b. The first and second lower flaps 21a, 21b and likewise the first and second upper flaps 22a, 22b are retained in releasable overlapping engagement with one another by means of releasable fasteners, which in the present embodiment are conventional releasable hook and loop fasteners commercially available under the trade name VELCRO. The cloth forming the exterior of the internal boot 12 constitutes the loop material of the VELCRO fasteners and patches 24 affixed to the second lower and upper flaps 21b, 22b at appropriate locations thereon constitute the hook material of the VELCRO fasteners.

The anterior of the internal boot 12 is further provided with an additional flap, i.e., an enclosure flap 25, which is attached to an anterior side of the heel portion 19 of the internal boot 12. The enclosure flap 25 tucks under the opposite anterior side of the heel portion 19 when the lower flaps 21a, 21b and the upper flaps 22a, 22b are placed in overlapping engagement with one another. The enclosure flap 25 covers any gaps which may occur in the continuity of the enclosure formed by closing the lower flaps 21a, 21b and the upper flaps 22a, 22b over one another in the above-described manner. The enclosure flap 25 also supplements the cushioning provided by the lower flaps 21a, 21b and the upper flaps 22a, 22b.

The internal boot 12 is transitioned from the closed on-the-leg configuration back to the open off-the-leg configuration by selectively disengaging the lower flaps 21a, 21b and the upper flaps 22a, 22b from releasable overlapping engagement with one another. In particular, the releasable VELCRO fasteners are uncoupled, the first lower flap 21a is pulled apart from the second lower flap 21b and the first upper flap 22a is pulled apart from the second upper flap 22b. The enclosure flap 25 is also untucked from under the opposite anterior side of the heel portion 19 and pulled away therefrom. Pulling apart the flaps 21a, 21b, 22a, 22b, 25 opens up the anterior of the internal boot 12, thereby exposing the interior 23 of the internal boot 12 so that the lower limb 11 can be withdrawn therefrom.

Figures 4, 9:
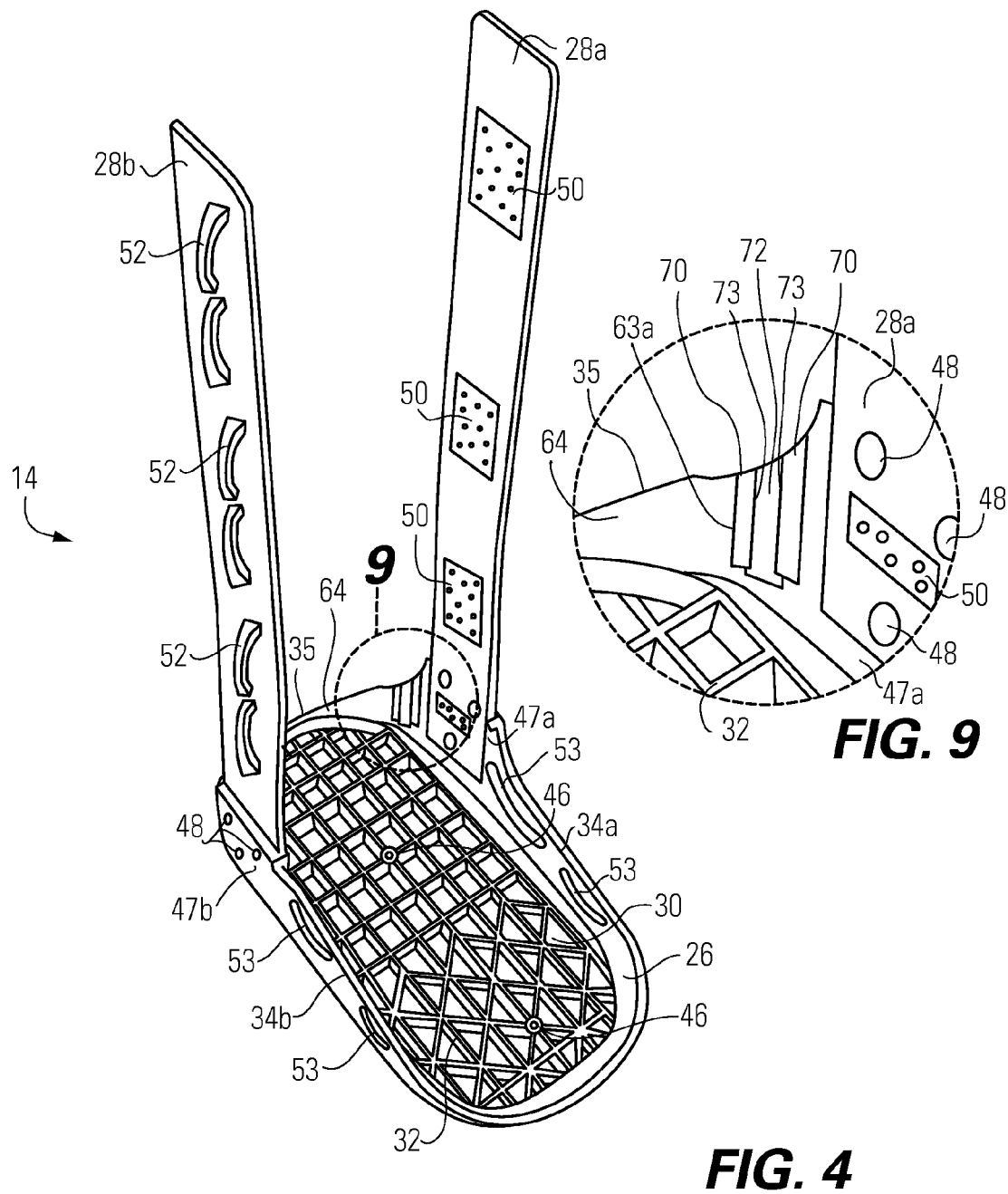
FIG. 4 is a front perspective view of an external shell included in the orthopedic walker boot of FIG. 1.
FIG. 9 is an enlarged partial view of the heel plate retention segment of the external shell of FIG. 4.

With continuing reference to FIGS. 1 and 2 and additional reference to FIG. 4, the external shell 14 of the orthopedic walker boot 10 is sized and configured in correspondence with the internal boot 12. In particular, the external shell 14 is sized and configured to receive the internal boot 12 in close fitting relationship into the external shell 14 when the internal boot 12 is in the closed on-the-leg configuration with the lower limb 11 disposed therein.

The external shell 14 comprises a base assembly 26 and first and second uprights 28a, 28b. The elements 26, 28a, 28b of the external shell 14 are formed from a hard rigid material, such as metal, molded plastic, or fiberglass, which is preferably further characterized as being high-strength and light-weight. The terms "pliant" and "rigid" as used herein are relative terms. A rigid material, such as the material of the external shell 14, has sufficient stiffness to substantially support and/or immobilize the lower limb 11 so that a wearer having the affected lower limb 11 can engage in low-impact activities such as walking or standing without substantially stressing or otherwise further negatively affecting the lower limb 11. Conversely, a pliant material, such as the material of the internal boot 12, by itself does not sufficiently support and/or immobilize the lower limb 11 to provide the affected lower limb 11 with substantial independent rehabilitative benefit.

The base assembly 26 is a unitary structure having an outer sole 30, a rib network 32, first and second sidewalls 34a, 34b and a heel plate retention segment 35. The outer sole 30 is a continuous piece extending along the bottom of the base assembly 26 and generally dimensioned in correspondence with the length and width of the foot. As such, the outer sole 30 extends essentially the entire length of the foot portion 16 of the internal boot 12 when the orthopedic walker boot 10 is worn on the lower limb 11. The bottom of the outer sole 30 preferably includes a layer of an elastomeric material which forms a walking surface 36 of the outer sole 30. The walking surface 36 has a tread pattern formed thereon to enhance the traction of the walking surface 36. The rib network 32 extends from the top of the outer sole 30 to enhance the structural rigidity of the outer sole 30. The rib network 32 prevents substantial flexion of the outer sole 30 when functioning as a walking platform.

Figure 5:
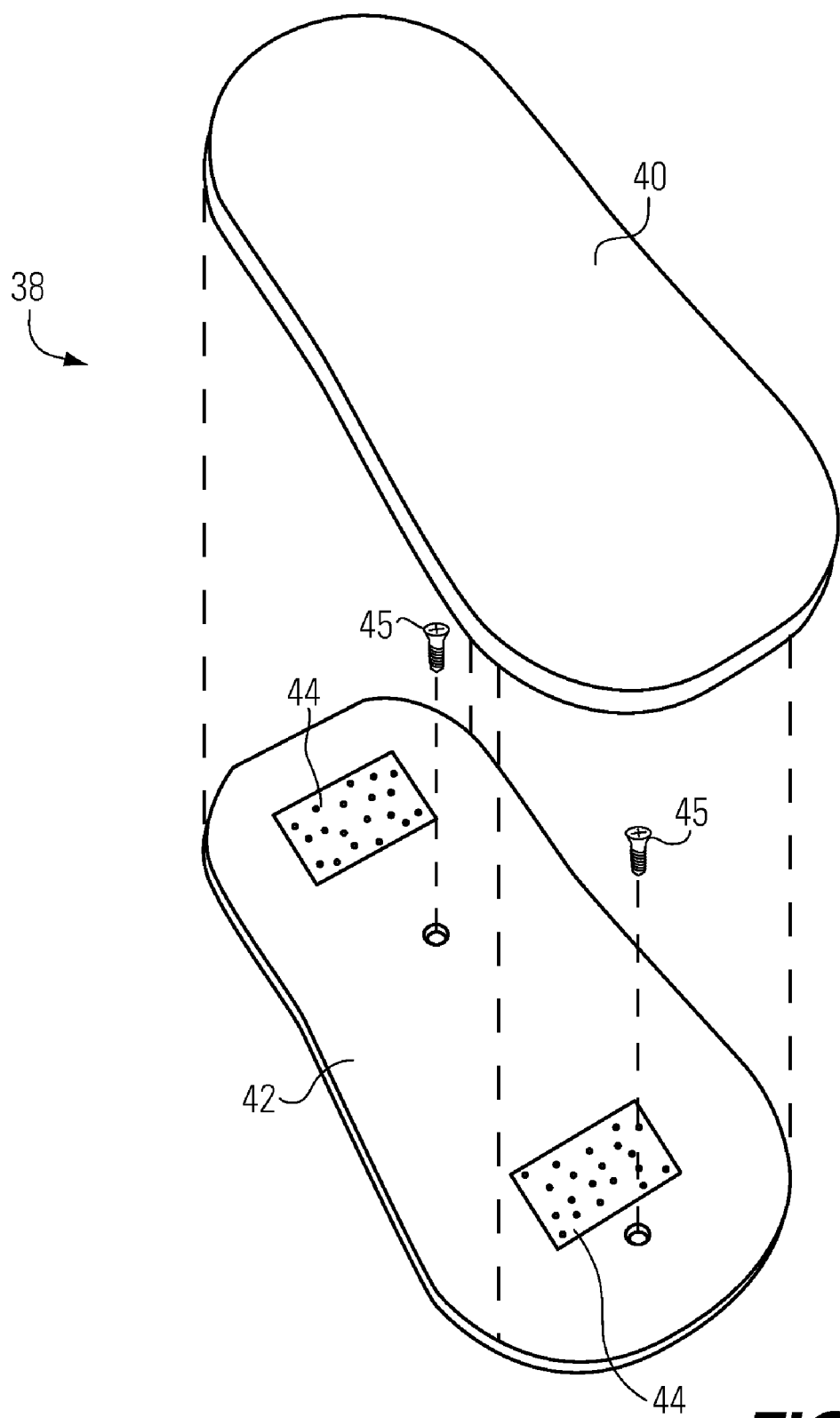
FIG. 5 is an exploded front perspective view of an insole included in the orthopedic walker boot of FIG. 1.

Referring additionally to FIG. 5, an insole 38 is preferably positioned atop the rib network 32 opposite the outer sole 30 to supplement the cushioning of the internal boot 12 along the sole of the foot of the wearer when the orthopedic walker boot 10 is worn on the lower limb 11. The insole 38 is generally dimensioned in correspondence with the outer sole 30. The insole 38 has two layers a cushion layer 40 positioned atop a stiffened layer 42. The cushion layer 40 is preferably formed from a cloth-foam-cloth laminate and the stiffened layer 42 is preferably formed from a flexible plastic which is substantially stiffer than the cushion layer 40. Releasable VELCRO fasteners are provided to retain the stiffened layer 42 in engagement with the cushion layer 40. The cloth forming the exterior of the cushion layer 40 constitutes the loop material of the VELCRO fasteners and patches 44 affixed to the stiffened layer 42 at appropriate locations thereon constitute the hook material of the VELCRO fasteners. Threaded screw fasteners 45 are also provided which extend through the stiffened layer 42 and fasten the stiffened layer 42 to the rib network 32 by means of correspondingly threaded screw holes 46 formed in the rib network 32.

With continuing reference to FIG. 4, the first and second sidewalls 34a, 34b are positioned at the opposing medial and lateral sides of the outer sole 30, respectively, adjacent to the ankle when the orthopedic walker boot 10 is worn on the lower limb 11. The heel plate retention segment 35 is posteriorly positioned on the base assembly 26 and extends above and along the posterior perimeter of the outer sole 30 between the first and second sidewalls 34a, 34b. The heel plate retention segment 35 is essentially perpendicular to the outer sole 30.

The first and second sidewalls 34a, 34b extend relatively higher than the heel plate retention segment 35 above and along the perimeter of the outer sole 30 from the medial and lateral sides thereof. The first and second sidewalls 34a, 34b are likewise essentially perpendicular to the outer sole 30. The first sidewall 34a has a first mount 47a formed thereon, to which the first upright 28a is fixably attached by fixable fasteners 48, such as rivets. The second sidewall 34b similarly has a second mount 47b formed thereon, to which the second upright 28b is fixably attached by fixable fasteners 48. As such, the first and second mounts 47a, 47b provide substantially immobile joints between the first upright and sidewall 28a, 34a and the second upright and sidewall 28b, 34b, respectively.

The first and second uprights 28a, 28b extend upward from the first and second mounts 38a, 38b, respectively, essentially the entire length of the leg portion 18 of the internal boot 12 when the internal boot 12 is positioned within the external shell 14. Releasable VELCRO fasteners are provided to retain the leg portion 18 of the internal boot 12 in engagement with the first and second uprights 28a, 28b of the external shell 14. The cloth forming the exterior of the internal boot 12 constitutes the loop material of the VELCRO fasteners and patches 50 affixed to the inside faces of the first and second uprights 28a, 28b at appropriate locations thereon constitute the hook material of the VELCRO fasteners.

The external shell 14 further comprises a plurality of paired strap guides 52 and a plurality of paired strap slots 53. The strap guides 52 are affixed to the first and second uprights 28a, 28b with one strap guide 52 of each pair affixed to the first upright 28a and the other strap guide 52 of the same pair affixed to the opposing second upright 28b. The strap slots 53 are formed in the first and second sidewalls 34a, 34b with one strap slot 53 of each pair formed in the first sidewall 34a and the other strap slot 53 of the same pair formed in the opposing second sidewall 34b.

With continuing reference to FIGS. 1 and 2, the external shell 14 is also provided with a plurality of retention straps 54 which are among the non-rigid elements of the substantially rigid external shell 14. Each retention strap 54 has two ends. A strap loop 56 is fixably attached to one end of the retention strap 54 while the opposite end of the retention strap 54 is free. The free end of each retention strap 54 is threaded either through a pair of the strap guides 52 or a pair of the strap slots 53 such that each pair of the strap guides 52 and the strap slots 53 retains a retention strap 54 therein. The retention strap 54 is constructed from a loop material and a tab 58 of hook material is fixably attached to the free end of each retention strap 54. As such, each retention strap 54 and hook tab 58 in combination cooperatively defines a VELCRO fastener.

In order for the external shell 14 to receive the internal boot 12 therein, it is necessary to open the anterior of the external shell 14. The anterior is opened by maintaining the retention straps 54 threaded through their respective pair of strap guides 52 or strap slots 53, but in a fully slackened condition. Once the internal boot 12 is placed in the external shell 14 through its open anterior, the anterior of the external shell 14 is closed by tightening and fastening the retention straps 54 which is effected by pulling the free tab end of each retention strap 54 across the anterior of the external shell 14 and threading the tab end through the strap loop 56 attached to the opposite end of the retention strap 54. The tab end of the retention strap 54 is then doubled back over the length of the retention strap 54 which extends across the anterior of the external shell 14 and tensioned until a desired degree of tightness is attained. The hook tab 58 of the retention strap 54 is releasably attached to a desired point on the underlying surface of the length of the retention strap 54 extending across the anterior of the external shell 14. In this manner, the retention straps 54 securely retain the internal boot 12 within the external shell 14, thereby enabling the external shell 14 to function as a rigid support frame for the pliant internal boot 12.

Figure 6:
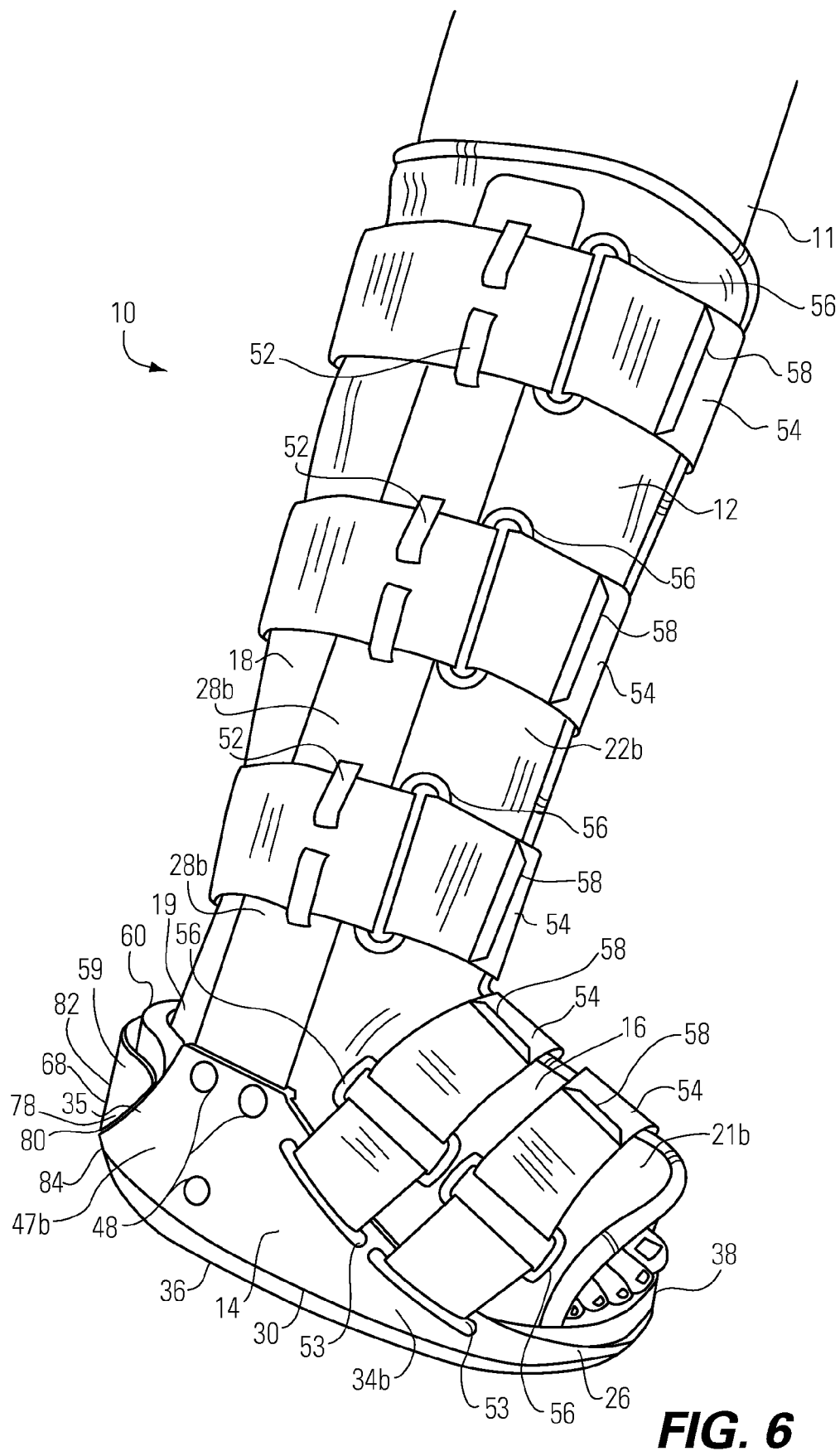
FIG. 6 is a side perspective view of the orthopedic walker boot of FIG. 1, but wherein the orthopedic walker boot has a closed-heel configuration.
Figure 7:
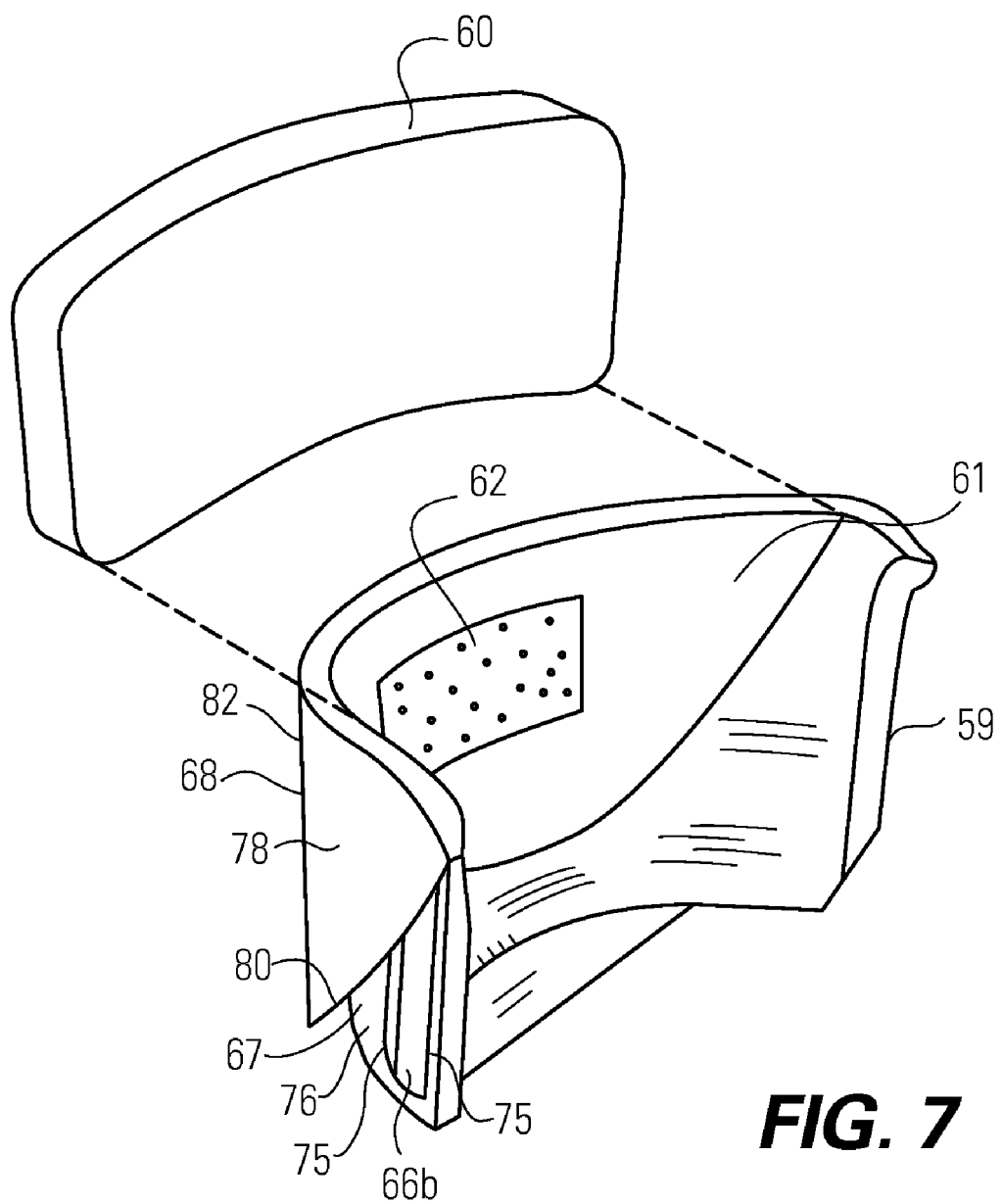
FIG. 7 is a front perspective view of a heel plate included in the orthopedic walker boot of FIG. 6.
Figure 8:
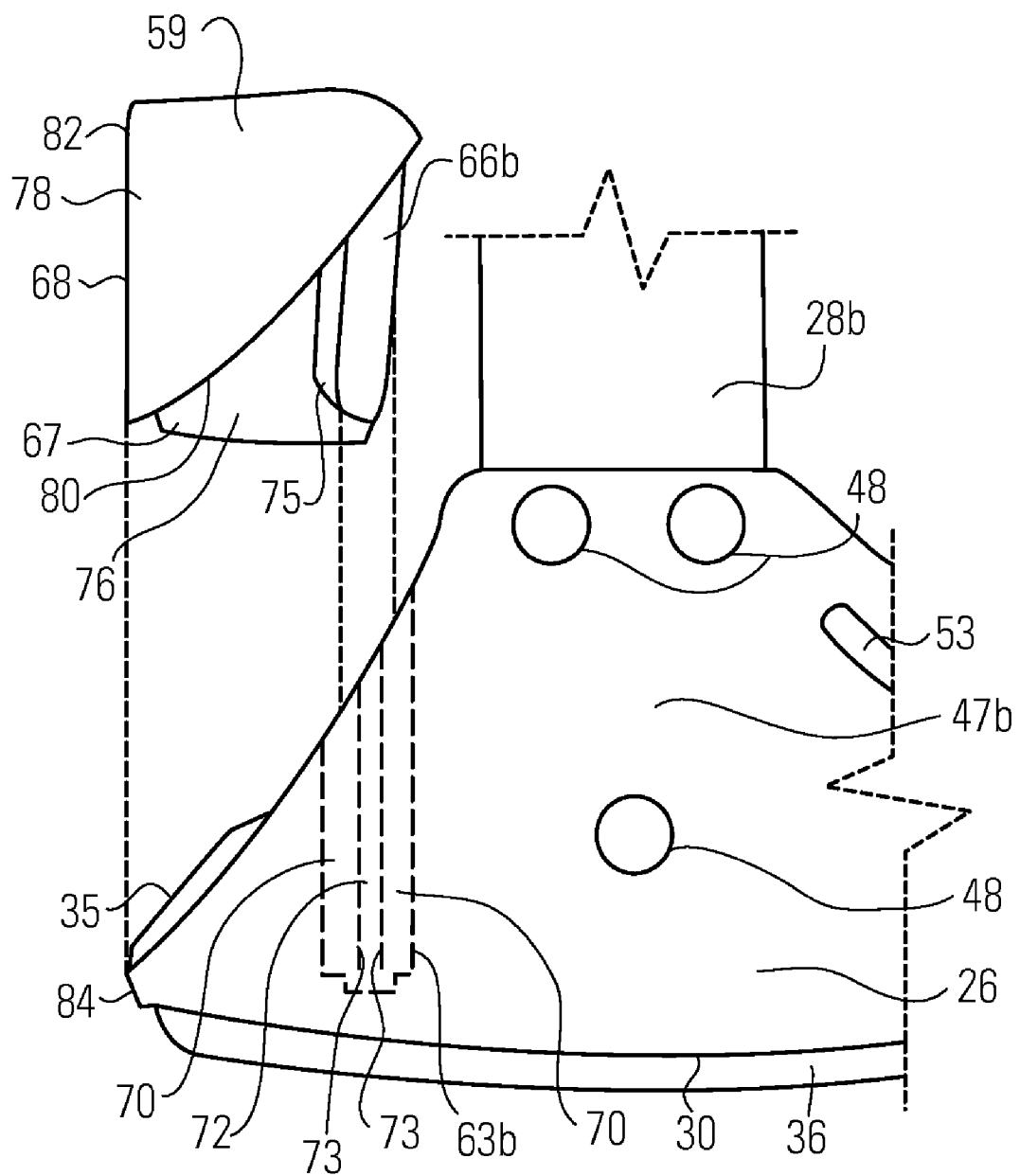
FIG. 8 is an exploded side elevational view of the heel plate and a heel plate retention segment of the external shell included in the orthopedic walker boot of FIG. 6.
Figure 10:
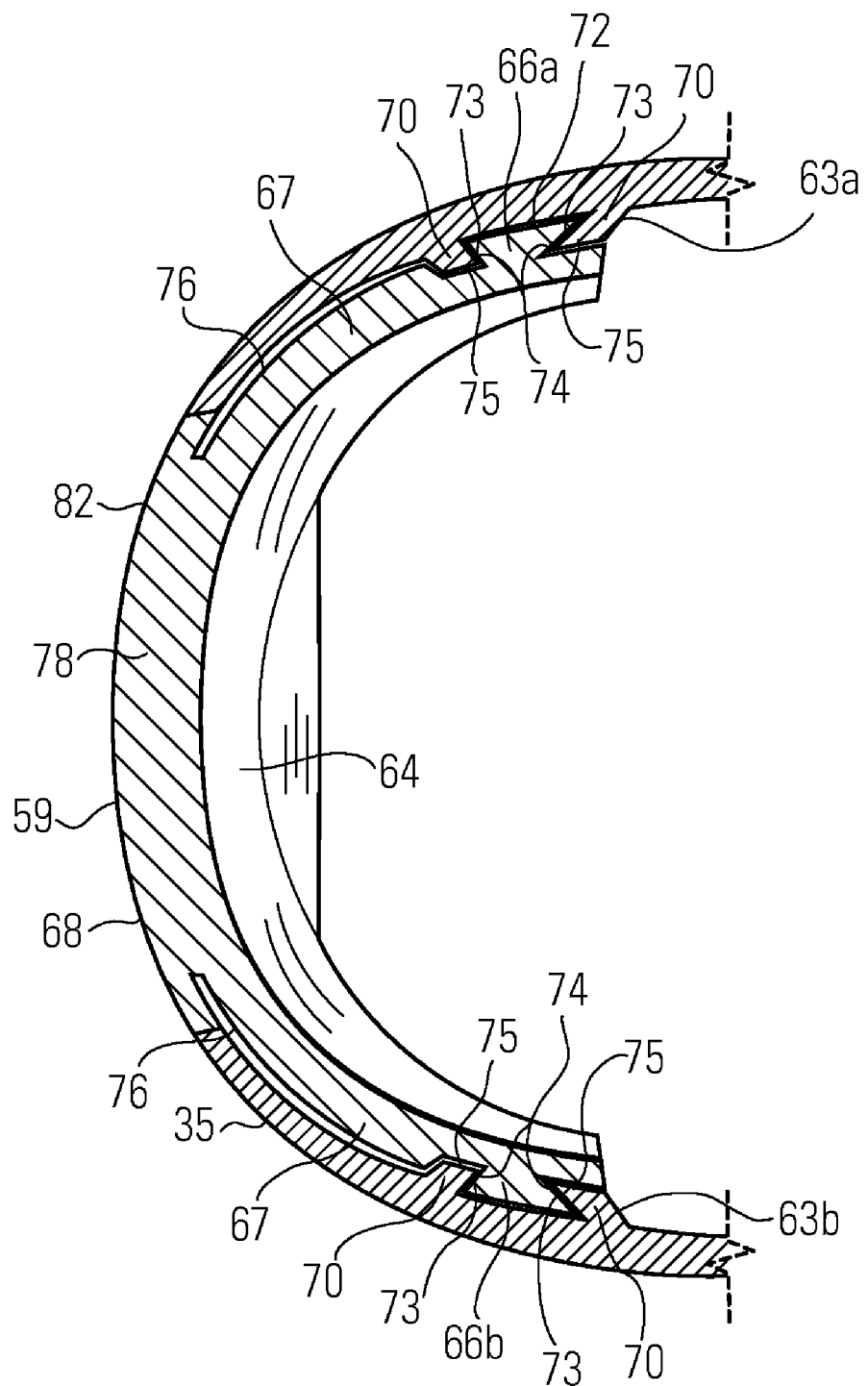
FIG. 10 is a downward-facing cross-sectional view of the assembled heel plate and heel plate retention segment of the external shell included in the orthopedic walker boot of FIG. 6 which is taken partway down the heel plate.

In accordance with the present embodiment, the orthopedic walker boot 10, and specifically the external shell 14, have two selectively interchangeable configurations. FIGS. 1 and 4 both show the orthopedic walker boot 10, and specifically the external shell 14, in an open-heel configuration. FIG. 6 shows the same orthopedic walker boot 10 as FIG. 1, but in a closed-heel configuration. The closed-heel configuration of the orthopedic walker boot 10 is characterized by the attachment of a separate heel plate 59, which is selectively attachable or detachable, to the structure of the external shell 14. Accordingly, when the orthopedic walker boot 10 is in the closed-heel configuration, the heel plate 59 is in an attached condition, i.e., the heel plate 59 is posteriorly mounted on the external shell 14 as an optional supplemental structure. In contrast, when the orthopedic walker boot 10 is in the open-heel configuration shown in FIGS. 1 and 4, the heel plate 59 is in a detached condition, i.e., the heel plate 59 is omitted altogether from the structure of the external shell 14.

With reference to FIGS. 6-10, the heel plate 59 is preferably formed as a unitary structure from the same hard rigid material as the remainder of the external shell 14. A heel pad 60 configured in correspondence with the inside face of the heel plate 59 is releasably attached to the inside face 61 of the heel plate 59 by means of a releasable VELCRO fastener which comprises a patch of loop material (not shown) affixed to the heel pad 60 and a patch of hook material 62 affixed to the inside face 61 of the heel plate 59 or vice versa. The heel pad 60 is preferably formed from a pliant foam material which supplements the cushioning of the internal boot 12 at the heel of the wearer when the orthopedic walker boot 10 is worn on the lower limb 11. It is noted that the heel pad 60 is omitted from FIG. 10 for clarity.

Posteriorly mounting the heel plate 59 on the external shell 14 is enabled by two tracks 63a and 63b formed on the inside face 64 of the heel plate retention segment 35 at each medial and lateral end thereof and two corresponding cooperative guide runners 66a and 66b formed on a recessed lower portion 67 of the outside face 68 of the heel plate 59 at each medial and lateral end thereof. Each track 63a, 63b of the heel plate retention segment 35 comprises a pair of rails 70 preferably integrally formed with and protruding from the inside face 64 of the heel plate retention segment 35. The two rails 70 of each track 63a, 63b are spaced slightly apart from one another as the rails 70 extend longitudinally vertically in parallel relation to one another along the inside face 64 of the heel plate retention segment 35.

The space between the two rails 70 defines a female retention slot 72 which is vertically bounded on either side by the respective longitudinal inside face 73 of each rail 70. The inside faces 73 of the rails 70 are beveled in relation to the inside face 64 of the heel plate retention segment 35 such that the horizontal cross-section of the retention slot 72 has an essentially trapezoidal configuration.

Each guide runner 66a, 66b of the heel plate 59 comprises a single runner preferably integrally formed with and protruding from the recessed lower portion 67 of the outside face 68 of the heel plate 59 and extends longitudinally and vertically along the lower portion 67 of the outside face 68. The inside faces 74 of each guide runner 66a, 66b are beveled in relation to the inside face 64 of the heel plate retention segment 35, but in the opposite direction as the beveled inside faces 73 of the rails 70. Accordingly, the retention slots 72 and guide runners 66a, 66b are correspondingly sized and configured relative to one another such that each female retention slot 72 is able to slidably receive and retain the respective male guide runner 66a, 66b therein when the practitioner desires to effect releasable attachment of the heel plate 59 to the heel plate retention segment 35.

A pair of clearance indentations 75 are also provided in the recessed lower portion 67 of the outside face 68 of the heel plate 59 adjacent to the guide runner 66a, 66b. The clearance indentations 75 are sized and configured in correspondence with the rails 70 such that the clearance indentations 75 are able to slidably receive an adjacent rail 70 when the guide runner 66a, 66b is received in the retention slot 72, thereby facilitating close fitting engagement of the heel plate 59 with the heel plate retention segment 35. The recessed configuration of the lower portion 67 of the outside face 68 of the heel plate 59 also enables the outside surface 76 of the lower portion 67 to slide into close fitting engagement with the inside face 64 of the heel plate retention segment 35 when the guide runner 66a, 66b is received in the retention slot 72, thereby further facilitating close fitting engagement of the heel plate 59 with the heel plate retention segment 35.

When the heel plate 59 is in the attached condition posteriorly mounted on the external shell 14, the outside face 68 of the heel plate 59 has a protruding upper portion 78 which extends upwardly away from the heel plate retention segment 35 essentially perpendicular to the outer sole 30. The protruding upper portion 78 of the outside face 68 has a bottom edge 80 which is aligned and continuously engaged with the posterior top edge of the heel plate retention segment 35. The upper portion 78 of the outside face 68 of the heel plate 59 also has an outside surface 82 which extends above and is continuous with the outside face 84 of the heel plate retention segment 35. Accordingly, the outside surface 82 of the upper portion 78 and the outside face 84 of the heel plate retention segment 35 form a smooth continuous surface on the posterior of the orthopedic walker boot 10.

The heel plate 59 in the attached condition covers, either entirely or at least partially, the heel portion 19 of the internal boot 12 and the heel of the lower limb 11 disposed therein. As such, the heel plate 59 provides a strong impact-resistant rigid protective cover for the posterior face of the wearer's heel, which substantially supplements the limited protection afforded by the heel portion 19 of the pliant internal boot 12.

It is particularly advantageous to use the closed-heel configuration of the orthopedic walker boot 10 where the wearer commonly participates in everyday activities which could otherwise lead to potentially painful impacts against the heel from objects in the external surroundings.

Figure 11:
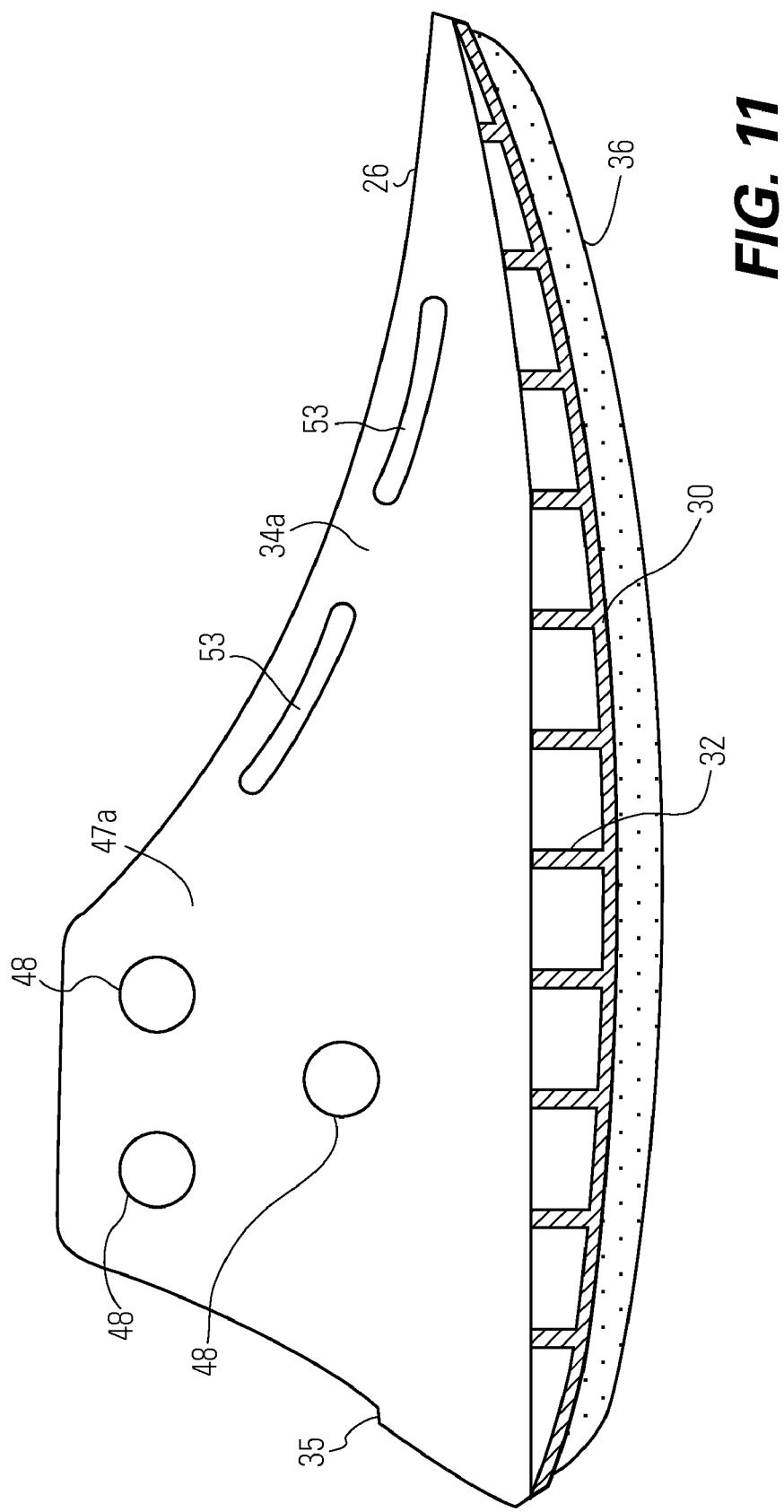
FIG. 11 is a cross-sectional view of the outer sole of the external shell included in the orthopedic walker boot of FIG. 1 which is taken along the longitudinal axis of the outer sole.
Figure 12:
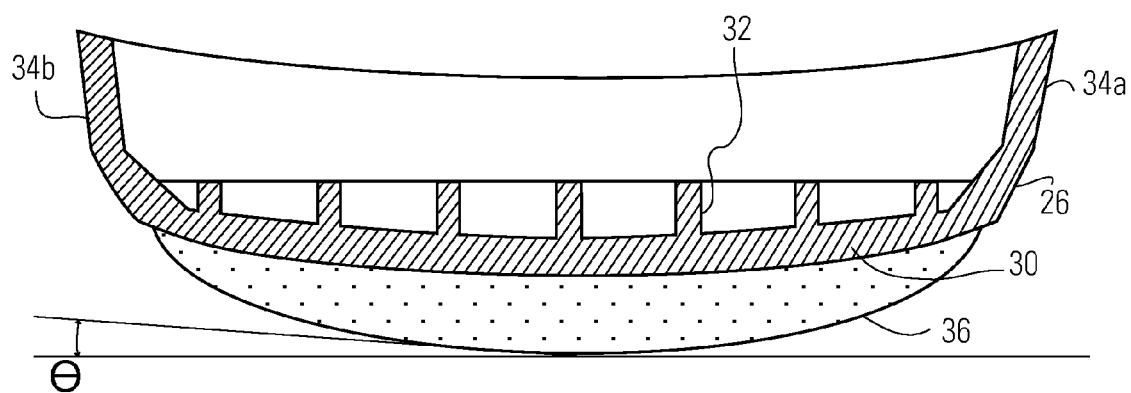
FIG. 12 is a cross-sectional view of the outer sole of the external shell included in the orthopedic walker boot of FIG. 1 which is taken along the latitudinal axis of the outer sole.

The orthopedic walker boot 10 of the present embodiment, and specifically the external shell 14, is further characterized as having two essentially perpendicular curved axes on the walking surface 36 of its outer sole 30 in the manner described below. Referring to FIGS. 11 and 12, the arcuate configuration of the walking surface 36 of the outer sole 30 is shown along two different axes. In particular, the walking surface 36 is curved along essentially the entire the length of its central longitudinal axis as shown in FIG. 11. The walking surface 36 is also curved along essentially the entire width of its central latitudinal axis, which is essentially perpendicular to the longitudinal axis, as shown in FIG. 12.

The degree of longitudinal curvature of the walking surface 36 is preferably essentially continuous and constant along its entire length. It is further noted that although the cross-sectional view of FIG. 11 is taken along the central longitudinal axis of the walking surface 36, this cross-sectional view would preferably appear essentially the same with respect to longitudinal curvature if taken along any other longitudinal line through the walking surface 36 away from, but parallel to, the central longitudinal axis. Similarly, the degree of latitudinal curvature of the walking surface 36 is preferably essentially continuous and constant along its entire width. Although the cross-sectional view of FIG. 12 is taken along the central latitudinal axis of the walking surface 36, this cross-sectional view would also preferably appear essentially the same with respect to latitudinal curvature if taken along any other latitudinal line through the walking surface 36 away from, but parallel to, the central latitudinal axis.

Constructing the outer sole 30 of the external shell 14 with two curved axes on its walking surface 36 beneficially facilitates both the longitudinal and latitudinal rolling of the foot in the normal walking gait when one is engaged in walking activity while wearing the orthopedic walker boot 10 on a lower limb 11. In some cases, only a slight degree of curvature in the axes achieves the desired benefit. For example, in accordance the embodiment shown in FIG. 12, a beneficial effect is achieved when the curvature of the latitudinal axis is characterized by only a slight angle $\theta$ of 2° as one moves latitudinally away from the longitudinal center line of the walking surface 36.

Referring to FIGS. 13-18, an alternate embodiment of the orthopedic walker boot of the present invention is shown and generally designated 110. The orthopedic walker boot 110 is sized and configured to be worn on a lower limb 11 of a person in substantially the same manner as the embodiment of the orthopedic walker boot 10 shown in FIGS. 1-12 and described above. The orthopedic walker boot 110 comprises an internal boot 112 and an external shell 114. The external shell 114 has substantially the same construction as the external shell 14 described above. Accordingly, the description of the external shell 14 set forth above applies equally to the external shell 114 of the present embodiment and the common elements of the external shell 114 are designated by the same reference characters as those of the external shell 14.

Figure 13:
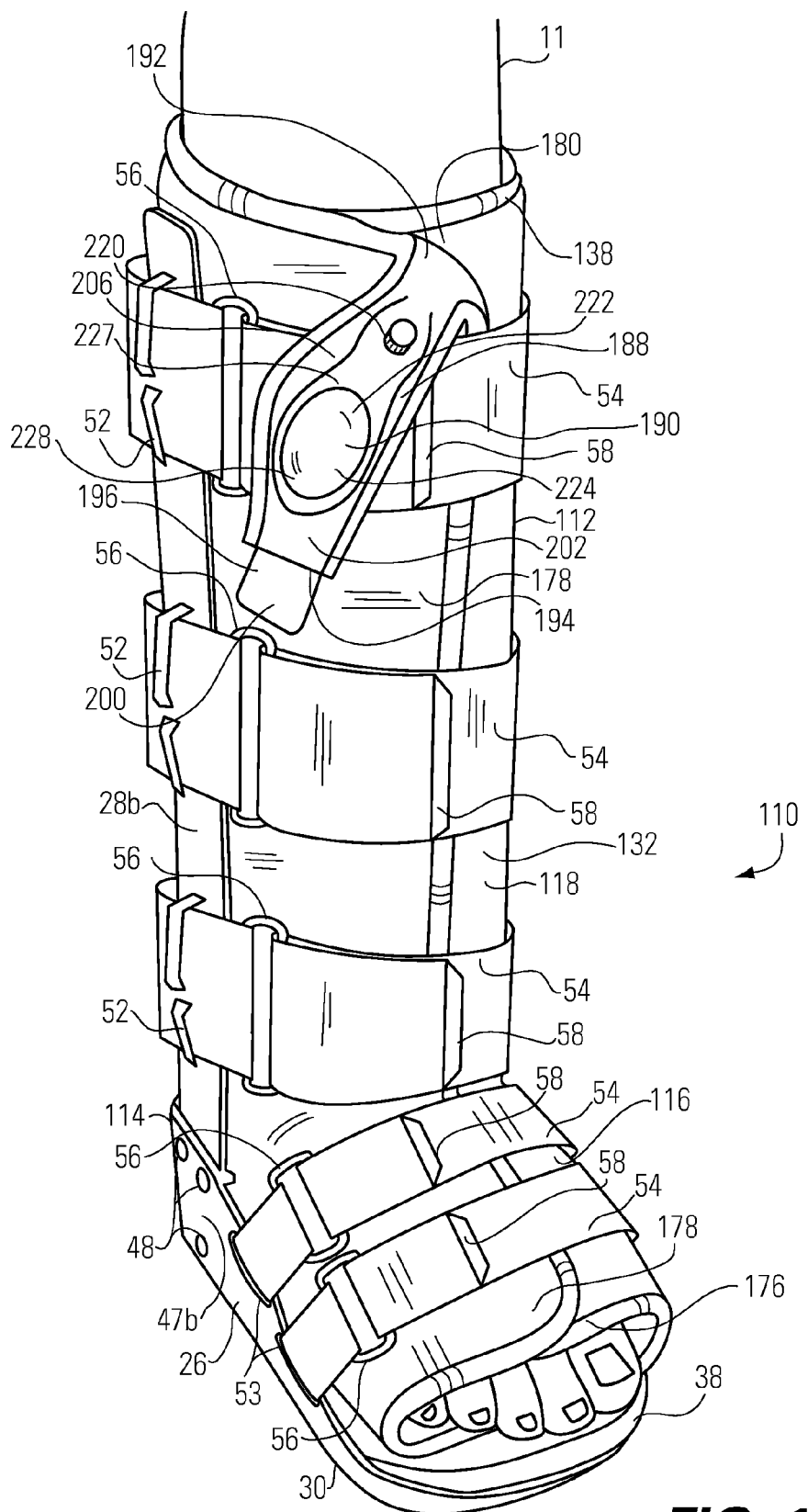
FIG. 13 is a front perspective view of an alternate embodiment of the orthopedic walker boot of the present invention worn on a lower limb, wherein the internal boot of the orthopedic walker boot includes a pump and a pair of inflatable bladders.
Figure 14:
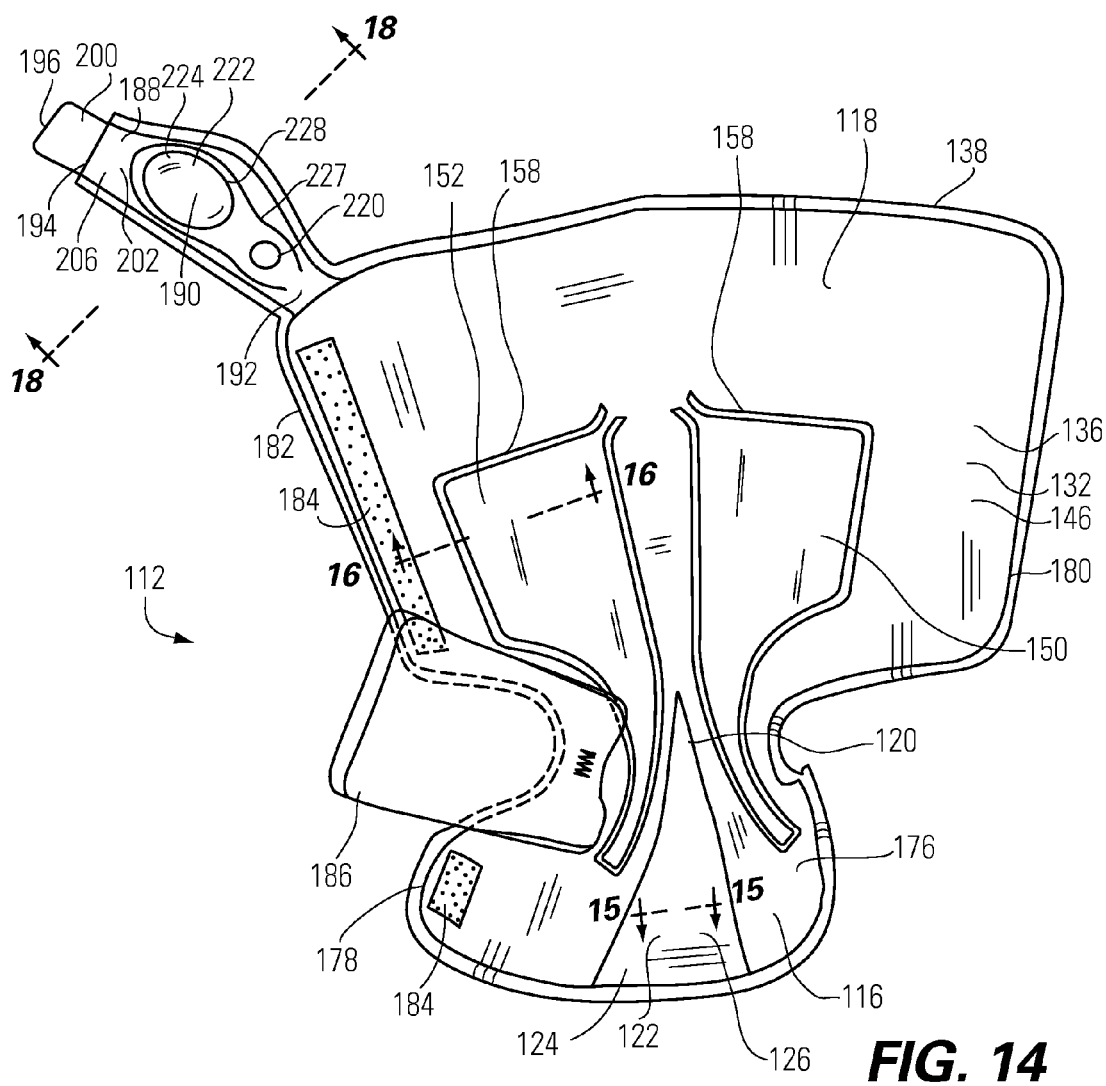
FIG. 14 is a front perspective view of the internal boot included in the orthopedic walker boot of FIG. 13, but with the internal boot having an off-the-leg configuration.

There are also a number of commonalities between the construction of the internal boot 112 and the construction of the internal boot 12. Referring initially to FIGS. 13 and 14, the internal boot 112 has a closed on-the-leg configuration shown in FIG. 13 and an open off-the-leg configuration shown in FIG. 14 which are essentially the same as those of the internal boot 12. The internal boot 112 likewise has a foot portion 116, a lower leg portion 118, and a heel portion 120 which bear essentially the same relation to one another and to the lower limb 11 as those of the internal boot 12 when the orthopedic walker boot 110 is worn on the lower limb 11 in the closed on-the-leg configuration. The internal boot 112 is also fabricated for the most part from soft pliant materials which insulate the enclosed lower limb 11 from direct contact with rigid objects external to the internal boot 112, thereby both cushioning and protecting the lower limb 11.

However, there are also several differences between the construction of the internal boot 112 and the construction of the internal boot 12 which are apparent from FIGS. 13-18 and the description below. With continuing reference to FIGS. 13 and 14, the internal boot 112 is fabricated from three panels of soft pliant material. The first panel is a sole panel 122 which is positioned at the bottom of the internal boot 112 under the sole of the foot when the internal boot 112 is worn on the lower limb 11. With additional reference to FIG. 15, the sole panel 122 is fabricated from a single laminate 124 which is characterized as a cloth-foam-cloth laminate having in series an inner cloth layer 126, a foam layer 128, and an outer cloth layer 130.

When used herein with reference to the elements of the internal boot 112 and the external shell 114, the terms "inner" and "outer" relate generally to the relative proximity of a given element to the lower limb 11 when the internal boot 112 is worn on the lower limb 11 and received in the external shell 114. An "inner" element is more proximal to the lower limb 11 than an "outer" element, which is more distal from the lower limb 11 than the "inner" element. As such, the inner cloth layer 126 of the sole panel laminate 124 engages the sole of the foot and the outer cloth layer 130 of the sole panel laminate 124 engages the insole 38 of the external shell 114 when the internal boot 112 is received therein while worn on the lower limb 11. The foam layer 128 of the sole panel laminate 124 resides between the inner and outer cloth layers 126, 130.

Figure 17:
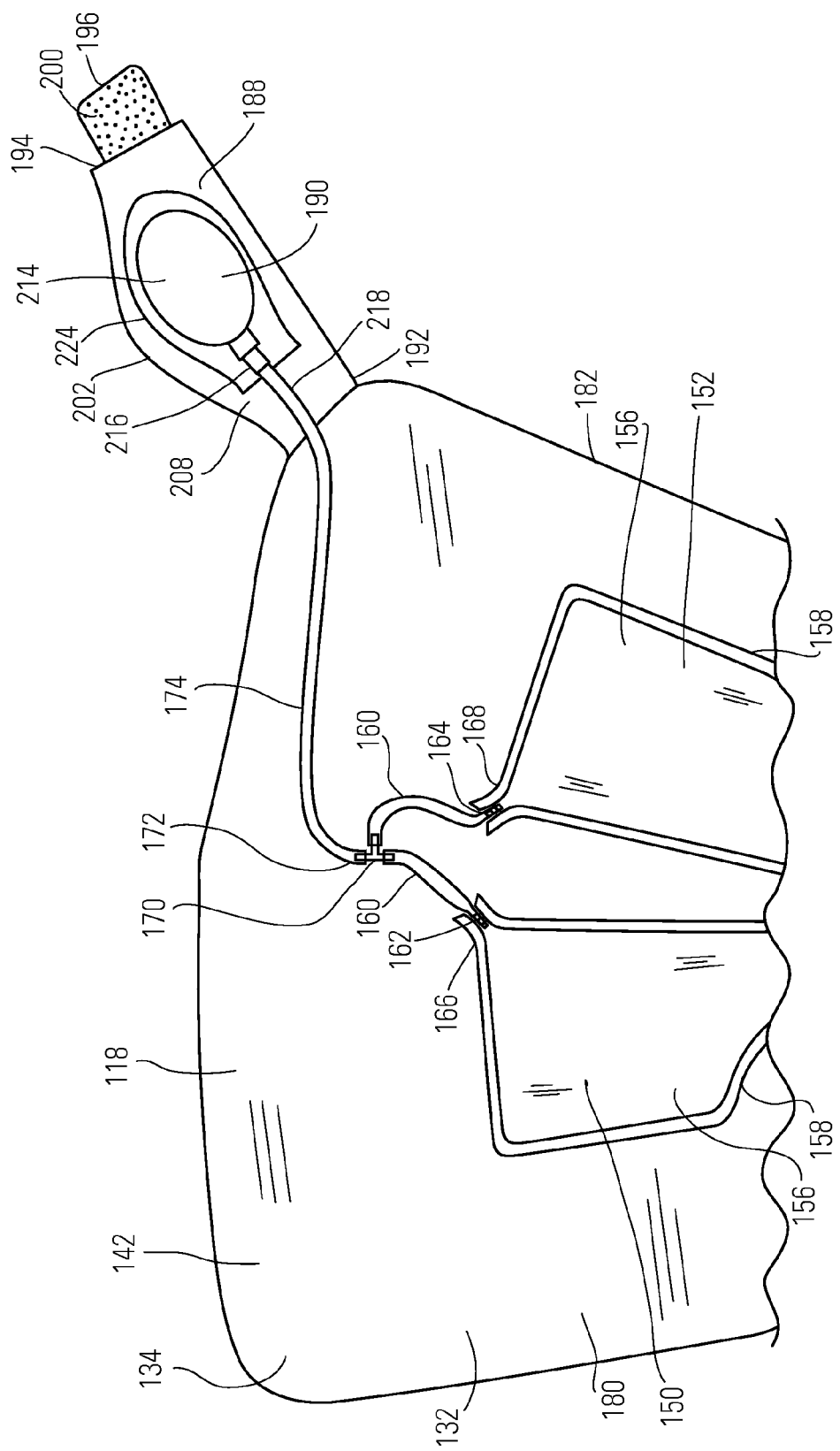
FIG. 17 is a partial rear view of the internal boot of FIG. 14, wherein the rear laminate cover of the internal boot is omitted to show the pump and bladders included within the internal boot.

Referring additionally to FIGS. 16 and 17, the second panel of the internal boot 112 is a leg panel 132 which makes up the bulk of the internal boot 112. The leg panel 132 has a relatively broad areal configuration. The leg panel 132 is positioned over the instep of the foot and wraps around the lower leg when the internal boot 112 is worn on the lower limb 11. The leg panel 132 is fabricated from two distinct laminates 134, 136 overlaying one another, but not bonded to one another except along their peripheral edges where they are sewn together with a cloth binding 138. The binding 138 also extends essentially continuously along the peripheral edges of the remainder of the internal boot 112 as shown in FIG. 14.

The first leg panel laminate 134 is an outer laminate characterized as a cloth-foam laminate having an outer cloth layer 140 and an inner foam layer 142. The second leg panel laminate 136 is an inner laminate characterized as a foam-cloth laminate having an outer foam layer 144 and an inner cloth layer 146. The outer laminate 134 engages the external shell 114 when the internal boot 112 is received therein. The outer cloth layer 140 of the outer laminate 134 forms the exteriorly exposed outer face of the internal boot 112 and is fabricated from a loop material of a VELCRO fastener. The outer cloth layer 140 fully covers and is continuously bonded with the inner foam layer 142 of the outer laminate 134.

The inner laminate 136 engages the instep and lower leg when the internal boot 112 is worn on the lower limb 11. The inner cloth layer 146 of the inner laminate 136 forms the interiorly exposed inner face of the internal boot 112. The inner cloth layer 146 fully covers and is continuously bonded with the outer foam layer 144 of the inner laminate 136. The cloth of the inner cloth layer 146 and the foam of the outer foam layer 144 are both formed from synthetic materials which render them weldable to one another or to other weldable materials by welding means, such as RF (radio frequency) welding, HF (high frequency) welding or the like. The outer foam layer 144 of the inner laminate 136 and the inner foam layer 142 of the outer laminate 134 abut one another at an interface 148, but are not bonded or otherwise attached to one another across this interface 148 except by the binding 138 at their peripheral edges as noted above.

The leg panel 132 additionally comprises a first bladder 150 and a second bladder 152 which are integrally formed with the inner laminate 136. In particular, the first and second bladders 150, 152 are incorporated into the outer face of the outer foam layer 144 of the inner laminate 136. Each bladder 150, 152 is constructed by cutting out an inner piece 154 and an essentially identically shaped outer piece 156 from a flexible clear plastic sheeting. The inner piece 154 is positioned atop the outer face of the outer foam layer 144 of the inner laminate 136 at an appropriate predetermined location thereon and the outer piece 156 is positioned atop the inner piece 154 with their peripheral edges aligned. The inner and outer pieces 154, 156 of plastic sheeting and the outer foam layer 144 and inner cloth layer 146 of the inner laminate 136 are all simultaneously welded together, preferably by RF (radio frequency) or HF (high frequency) welding, along essentially the entire length of the peripheral edges of the inner and outer pieces 154, 156. The resulting weld seam 158 is a unitary construct of thermally fused cloth, foam and plastic sheeting. The weld seam 158 acts as an airtight seal at the peripheral edges of the inner and outer pieces 154, 156 to define the perimeter of each bladder 150, 152.

The first and second bladders 150, 152 reside at the interface 148 of the inner laminate 136 and the outer laminate 134 and are symmetrically positioned with respect to one another on the opposing medial and lateral sides of the internal boot 112. As such, each bladder 150, 152 occupies a part of the foot, lower leg and heel portions 116, 118, 120 of the internal boot 112. The first and second bladders 150, 152 are in fluid communication with one another by means of a connective line 160 extending between them which likewise resides at the interface 148 between the inner and outer laminates 136, 134. The connective line 160 has a first end 162 and a second end 164 which are preferably welded or otherwise permanently bonded to ports 166, 168 in the first and second bladders 150, 152, respectively.

A tee fitting 170 is positioned in the connective line 160 and receives a first end 172 of an air inlet/outlet line 174 which is preferably welded or otherwise permanently bonded to the tee fitting 170. The air inlet/outlet line 174 is described in further detail below. With the exception of the first and second bladders 150, 152, the internal boot 112 is free of any supplemental support structures, such as stays, stiffeners, splints, or the like, which are integral with, mounted to, or otherwise associate with the internal boot 112.

The anterior of the leg panel 132 of the internal boot 112 is provided with a plurality of flaps which enable the practitioner to transition the internal boot 112 between an open off-the-leg configuration and a closed on-the-leg configuration in a manner described below. In particular, the anterior of the leg panel 132 has an inner lower flap 176 and an outer lower flap 178 which are integrally configured with the opposing vertical edges of the foot portion 116 of the internal boot 112. The anterior of the leg panel 132 additionally has an inner upper flap 180 and an outer upper flap 182 which are integrally configured with the opposing vertical edges of the lower leg portion 118 of the internal boot 112.

The inner and outer lower flaps 176, 178 and the inner and outer upper flaps 180, 182 are selectively engagable with one another and disengagable from one another by means of releasable VELCRO fasteners. In particular, the cloth forming the outer face of the inner lower and upper flaps constitutes the loop material of the VELCRO fastener and patches 184 formed from the hook material of the VELCRO fastener are affixed to the inner face of the outer lower and upper flaps 178, 182 near the vertical edge thereof.

The anterior of the leg panel 132 of the internal boot 112 also has an enclosure flap 186, which is attached to a vertical edge of the heel portion 120 of the internal boot 112. The enclosure flap 186 tucks under the opposing vertical edge of the heel portion 120 when the outer and inner lower flaps 176, 180 and the outer and inner upper flaps 178, 182 of the internal boot 112 are placed in overlapping engagement with one another as described below. The enclosure flap 186 covers any gaps which may occur in the continuity of the enclosure formed by closing the outer and inner lower flaps 178, 176 and the outer and inner upper flaps 182, 180 over one another. The enclosure flap 186 also supplements the cushioning provided by the outer and inner lower flaps 178, 176 and the outer and inner upper flaps 182, 180.

The third panel of the internal boot 112 is a pump panel 188 which houses a pump 190. The pump panel 188 has a relatively narrow elongate linear configuration with two ends. The first end 192 of the pump panel 188 is attached to and extends from an upper portion of the leg panel 132. More particularly, the first end 192 is permanently sewn or otherwise fixably attached to and extends from the top corner of the outer upper flap 182 on the leg panel 132 of the internal boot 112. The opposite second end 194 of the pump panel 188 has a hook tab 196 sewn thereto. A first side 198 of the hook tab 196 has an exposed face of the hook material of a VELCRO fastener and the opposite second side 200 of the hook tab 196 has a smooth face. The pump panel 188 and the pump 190 housed therein have a non-operational orientation and an operational orientation with respect to the internal boot 112 which are described below.

Figure 19:
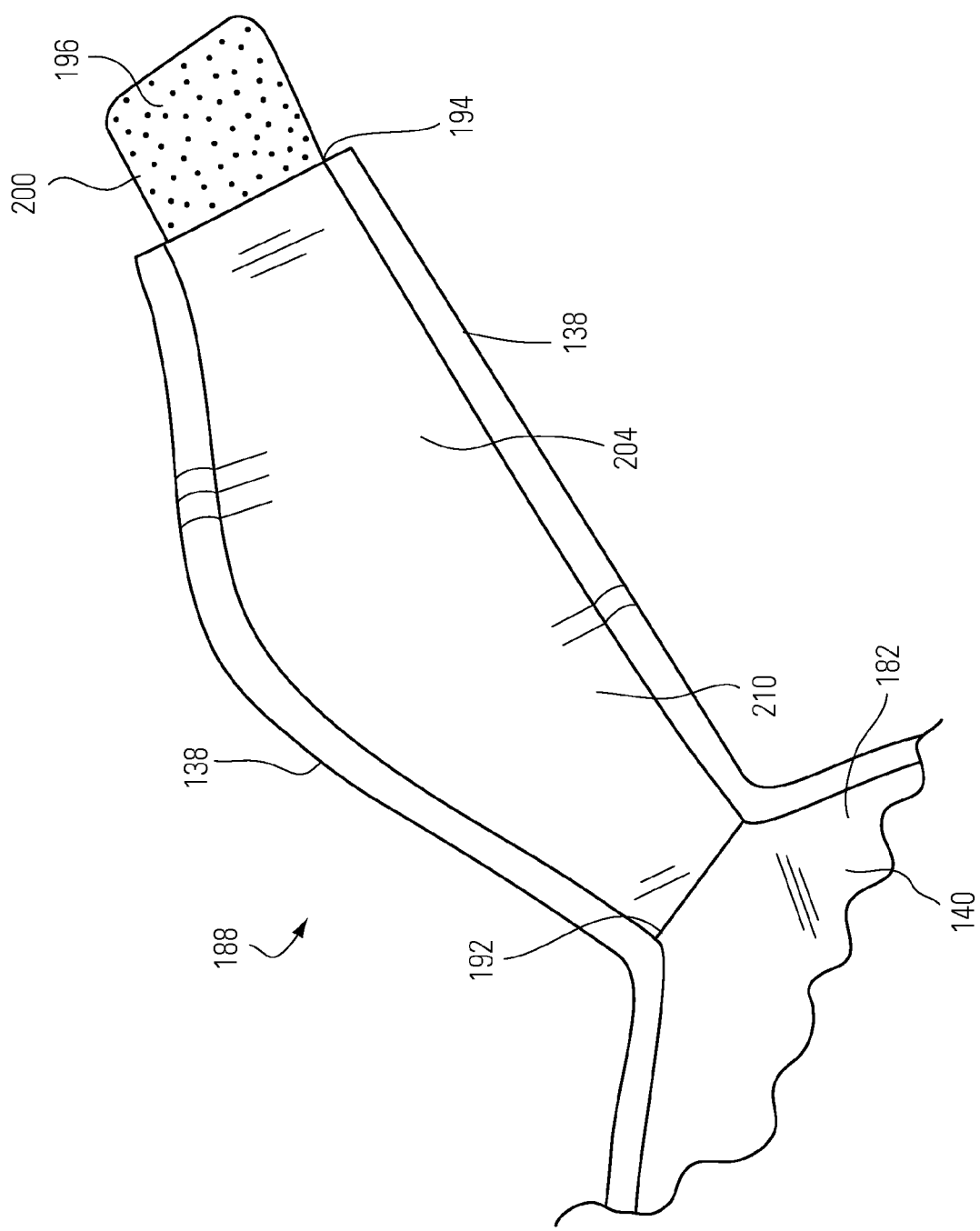
FIG. 19 is a rear view of the pump panel of the internal boot of FIG. 14.

Referring to FIGS. 13 and 14 and additionally to FIGS. 18 and 19, the pump panel 188 is fabricated from two distinct laminates 202, 204 overlaying one another in a manner similar to the leg panel 132. The first pump panel laminate 202 has a cloth layer 206 and a foam layer 208. The cloth layer 206 is on the inside of the pump panel 188 when the pump 190 and pump panel 188 are in the non-operational orientation and the internal boot 112 is in the open off-the-leg configuration. The second pump panel laminate 204 likewise has a cloth layer 210 and a foam layer 212. However, the cloth layer 210 is on the outside of the pump panel 188 when the pump 190 and pump panel 188 are in the non-operational orientation and the internal boot 112 is in the open off-the-leg configuration. In addition, the smooth face 200 of the hook tab 196 is on the inside of the pump panel 188 and the hook material 198 is on the outside of the pump panel 188 which enables the hook tab 196 to hang free when the pump 190 and pump panel 188 are in the non-operational orientation and the internal boot 112 is in the open off-the-leg configuration.

The pump 190 is positioned between the first and second pump panel laminates 202, 204 and comprises a squeeze bulb 214 and an air inlet/outlet valve 216 which is preferably permanently bonded or otherwise permanently affixed to the squeeze bulb 214 in fluid communication therewith. The air inlet/outlet valve 216 receives a second end 218 of the air inlet/outlet line 174 which is likewise preferably permanently bonded or otherwise permanently affixed to the air inlet/outlet valve 216. As such, the air inlet/outlet line 174 extends from the pump 190 in the pump panel 188 to the tee fitting 170 in the leg panel 132 and provides fluid communication between the air inlet/outlet valve 216 and the first and second bladders 150, 152. The air inlet/outlet valve 216 has a knob 220 which is manually rotatable to transition the valve 216 between air inlet and air outlet modes of operation.

The pump 190 is retained in position between the first and second pump panel laminates 202, 204 by a pump pouch 222 which receives the pump 190 therein. A first side 224 of the pump pouch 222 is fabricated from a thin elastic cloth and the second side 226 is fabricated from a thicker elastic rubber-like material which serves as a backing for the pump 190. The first and second sides 224, 226 are sewn to one another along a seam 227 to form the pump pouch 222 and are likewise sewn to the first and second pump panel laminates 202, 204 along the seam 227 to secure the pump pouch 222 in the pump panel 188. A generally circular pump opening 228 is cut out of the first pump panel laminate 202 to expose the first side 224 of the pump pouch 222 and the underlying squeeze bulb 214. A knob opening (not shown) is similarly cut out of the first pump panel laminate 202 adjacent to the pump opening 228 to expose the knob 220 of the air inlet/outlet valve.

Fitting the internal boot 112 with the lower limb 11 of the wearer therein into the external shell 114 of the orthopedic walker boot 110 is effected in substantially the same manner as described above with reference to the orthopedic walker boot 10. However, before transitioning the internal boot 112 to the closed on-the-leg configuration, the knob 220 of the air inlet/outlet valve 216 is first manually rotated in a first direction to set the valve 216 in the outlet mode of operation. The outlet mode setting at least partially deflates the first and second bladders 150, 152 of the internal boot 112, thereby reducing the girth of the internal boot 112 when the internal boot 112 is transitioned to the closed on-the-leg configuration with the lower limb 11 disposed therein. Once the closed on-the-leg configuration of the internal boot 112 is achieved with the lower limb 11 of the wearer therein, the internal boot 112 is appropriately positioned in the external shell 114 and the retention straps 54 are tightened and fastened to secure the internal boot 112 to the external shell 114.

The pump 190 and pump panel 188 are switched from the non-operational orientation to the operational orientation when the internal boot 112 is in the closed on-the-leg configuration with the lower limb 11 of the wearer therein and is secured in the external shell 114. The operational orientation is effected by folding the pump panel 188 back over the outer face of the outer upper flap 182 on the leg panel 132 and over the intervening uppermost retention strap 54 on the external shell 114 to an angle of about 30° from vertical as shown in FIG. 13. The second end 194 of the pump panel 188 is then attached to the leg panel 132 and/or the external shell 114 in a manner described below. As such, the pump 190 and pump panel 188 are in an outer position relative to the leg panel 132 and the external shell 114 when the pump 190 and pump panel 188 are in the operational orientation It is apparent from the above that the positioning of the pump panel 188 in the operational orientation is reversed relative to the non-operational orientation. In particular, the second pump panel laminate 204 is positioned on the inside of the pump panel 188 adjacent to the outer face of the outer upper flap 182 on the leg panel 132. Conversely, the first pump panel laminate 202 is positioned on the outside of the pump panel 188, thereby positioning the pump opening 228 and knob 220 on the outside when the pump 190 and pump panel 188 are in the operational orientation. The smooth face 200 of the hook tab 196 is similarly positioned on the outside of the pump panel 188. Conversely, the hook material 198 of the hook tab 196 is positioned on the inside of the pump panel 188 adjacent to the loop material on the outer face of the outer upper flap 182 on the leg panel 132.

This position enables engagement of the hook material 198 on the hook tab 196 with the loop material of the leg panel 132 which is positioned directly beneath the hook tab 196 (i.e., in an inner position relative to the hook tab 196). Engagement of the hook and loop material correspondingly enables selective releasable attachment of the second end 194 of the pump panel 188 to the leg panel 132 with the pump panel 188 in an outer overlapping position relative to the leg panel 132 and the intervening uppermost retention strap 54 of the external shell 114. As a result of positioning the pump panel 188 outside the retention strap 54 and the leg panel 132, the squeeze bulb 214 and valve knob 220 of the pump 190 are outwardly exposed on the front of the walker boot 110, which facilitates access to the pump 190 by the practitioner and correspondingly facilitates operation of the pump 190.

Although not shown, it is alternatively within the purview of the skilled artisan and within the scope of the present invention to pivotally rotate the second end 194 of the pump panel 188 about the first end 192 in either a clockwise or counterclockwise direction away from the position of the second end 194 shown in FIG. 13 before releasably attaching the second end 194 to a select location on the walker boot 110. For example, if the second end 194 of the pump panel 188 is rotated about 30° in the counterclockwise direction away from the position shown in FIG. 13 to an essentially vertical position, the hook tab 196 is positioned in whole or in part directly over the next successive retention strap 54 below the uppermost retention strap 54. Since the next successive retention strap 54 is fabricated from a loop material, the second end 194 of the pump panel 188 is selectively releasably attached to the underlying retention strap 54 by hook and loop fastening means in addition to or in the alternative to attaching the second end 194 of the pump panel 188 to the leg panel 132.

In another example, if the second end 194 of the pump panel 188 is rotated about 15° in the clockwise direction away from the position shown in FIG. 13 to an angle about 45° from vertical, the hook tab 196 is positioned in whole or in part directly over the second upright member 28*b*. If a patch of loop material is fixably attached to the outside face of the second upright member 28*b*, the second end 194 of the pump panel 188 is selectively releasably attached to the underlying second upright member 28*b* of the external shell 114 by hook and loop fastening means in addition to or in the alternative to attaching the second end 194 of the pump panel 188 to the leg panel 132.

In yet another example, if the second end 194 of the pump panel 188 is rotated about 30° in the clockwise direction away from the position shown in FIG. 13 to an angle about 60° from vertical, the hook tab 196 is positioned in whole or in part directly over the uppermost retention strap 54. Since the uppermost retention strap 54 is fabricated from a loop material, the second end 194 of the pump panel 188 is selectively releasably attached to the underlying uppermost retention strap 54 by hook and loop fastening means in addition to or in the alternative to attaching the second end 194 of the pump panel 188 to the leg panel 132.

Regardless of the specific attachment location for the second end 194 of the pump panel 188, operation of the pump 190 is effected by manually rotating the knob 220 of the air inlet/outlet valve 216, in a second direction opposite the first to set the valve 216 in the inlet mode of operation. The squeeze bulb 214 is then alternately manually depressed and elastically expanded to inflate the first and second bladders 150, 152. Inflating the first and second bladders 150, 152 correspondingly increases the girth of the internal boot 112, thereby pressing the internal boot 112 against the relatively rigid support elements of the external shell 114. Once a desired snug fit is achieved for the internal boot 112 within the external shell 114, operation of the pump 190 is terminated and the first and second bladders 150, 152 maintain a fixed level of inflation. At this point, the walker boot 110 is properly fitted onto the lower limb 11 of the wearer and is in a suitable condition for the wearer to engage in normal everyday low-impact activities.

While the forgoing preferred embodiments of the invention have been described and shown, it is understood that alternatives and modifications, such as those suggested and others, may be made thereto and fall within the scope of the invention.

I claim:

1. An orthopedic walker boot comprising:
an internal boot having a closed on-the-leg configuration, said internal boot including a leg panel having an inflatable bladder and a pump panel having a pump for inflating said bladder, wherein said leg panel is configured to wrap around a leg of a wearer when said internal boot is in said closed on-the-leg configuration and said pump panel is configured with a first end and a second end, said first end fixably attached to said leg panel; and
an external shell sized and configured to receive said internal boot when in said closed on-the-leg configuration, wherein said second end of said pump panel is free when said pump panel is in a non-operational orientation and said pump panel is placed in an operational orientation by selectively and releasably attaching said second end of said pump panel to said leg panel or said external shell when said leg panel is in said closed on-the-leg configuration and said internal boot is received within said external shell such that said pump panel is in an overlapping outer position relative to said leg panel when in said operational orientation.

2. The orthopedic walker boot of claim 1, wherein said external shell is substantially rigid.

3. The orthopedic walker boot of claim 2, wherein said substantially rigid external shell includes a non-rigid retention strap.

4. The orthopedic walker boot of claim 3, wherein said pump panel is in an overlapping outer position relative to said retention strap of said external shell when said pump panel is in said operational orientation.

5. The orthopedic walker boot of claim 1, wherein said bladder is integrally formed with the remainder of said leg panel.

6. The orthopedic walker boot of claim 5, wherein said bladder and a cloth and foam laminate sheet are integrally welded together in said leg panel.

7. The orthopedic walker boot of claim 1, wherein said pump panel is in an overlapping outer position relative to said external shell when said pump panel is in said operational orientation.

8. The orthopedic walker boot of claim 1, wherein said pump panel has a relatively narrow elongate linear configuration and said leg panel has a relatively broad areal configuration.

9. The orthopedic walker boot of claim 1, wherein said pump panel is fixably attached to an upper portion of said leg panel and extends from said upper portion when said pump panel is in said non-operational orientation.

10. An orthopedic walker boot comprising:
an internal boot having an on-the-leg configuration and an off-the-leg configuration, said internal boot including a leg panel having an inflatable bladder and a pump flap having a pump for inflating said bladder, wherein said leg panel is configured to engage a leg of a wearer when said internal boot is in said on-the-leg configuration and wherein said pump flap has a first end attached to said leg panel and a second end selectively releasably attachable to said leg panel or said external shell; and an external shell configured to receive said internal boot when in said on-the-leg configuration, wherein said second end of said pump flap is unattached when transitioning said internal boot from said off-the-leg configuration to said on-the-leg configuration and wherein said second end of said pump flap is releasably attached to said leg panel or said external shell in an overlapping outer position relative to said leg panel when said internal boot is in said on-the-leg configuration received within said external shell.

11. The orthopedic walker boot of claim 10, wherein said external shell is substantially rigid.

12. The orthopedic walker boot of claim 10, wherein said external shell includes a retention strap.

13. The orthopedic walker boot of claim 12, wherein said pump flap is in an outer position relative to said retention strap of said external shell when said internal boot is in said on-the-leg configuration.

14. The orthopedic walker boot of claim 10, wherein said bladder is integrally formed with at least a portion the remainder of said leg panel.

15. The orthopedic walker boot of claim 10, wherein said bladder and a cloth and foam laminate sheet are integrally welded together in said leg panel.

16. The orthopedic walker boot of claim 10, wherein said pump flap has a relatively narrow elongate linear configuration and said leg panel has a relatively broad areal configuration.

17. The orthopedic walker boot of claim 10, wherein said pump flap is fixably attached to an upper portion of said leg panel with said second end unattached and extending from said upper portion when transitioning said internal boot from said off-the-leg configuration to said on-the-leg configuration.

* * * * *